(12) United States Patent
Robert et al.

(10) Patent No.: US 9,668,651 B2
(45) Date of Patent: Jun. 6, 2017

(54) OPHTHALMOLOGIC APPARATUS

(71) Applicant: KABUSHIKI KAISHA TOPCON, Itabashi-ku (JP)

(72) Inventors: Foster Robert, Escondido, CA (US); Ishihara Mutsutaka, Nerima-ku (JP)

(73) Assignee: KABUSHIKI KAISHA TOPCON, Itabashi-ku (JP)

( * ) Notice: Subject to any disclaimer, the term of this patent is extended or adjusted under 35 U.S.C. 154(b) by 49 days.

(21) Appl. No.: 14/724,411

(22) Filed: May 28, 2015

(65) Prior Publication Data

US 2015/0342459 A1    Dec. 3, 2015

Related U.S. Application Data

(60) Provisional application No. 62/004,583, filed on May 29, 2014.

(51) Int. Cl.

| A61B 3/10 | (2006.01) |
| A61B 3/18 | (2006.01) |
| A61B 3/04 | (2006.01) |
| A61B 3/02 | (2006.01) |
| A61B 3/06 | (2006.01) |
| A61B 3/00 | (2006.01) |
| A61B 3/032 | (2006.01) |
| A61B 3/103 | (2006.01) |
| A61B 3/107 | (2006.01) |

(Continued)

(52) U.S. Cl.
CPC .............. *A61B 3/18* (2013.01); *A61B 3/0033* (2013.01); *A61B 3/022* (2013.01); *A61B 3/032* (2013.01); *A61B 3/04* (2013.01); *A61B 3/063* (2013.01); *A61B 3/103* (2013.01); *A61B 3/102* (2013.01); *A61B 3/107* (2013.01); *A61B 3/12* (2013.01); *A61B 3/16* (2013.01)

(58) Field of Classification Search
USPC ........................................................ 351/205
See application file for complete search history.

(56) References Cited

U.S. PATENT DOCUMENTS

| 3,969,020 A | 7/1976 | Lynn et al. |
| 6,048,064 A | 4/2000 | Hosoi et al. |
| (Continued) | | |

FOREIGN PATENT DOCUMENTS

| EP | 1 932 465 A1 | 6/2008 |
| JP | 8-317904 | 12/1996 |
| JP | 4138432 | 8/2008 |

OTHER PUBLICATIONS

Extended European Search Report issued Oct. 19, 2015 in Patent Application No. 15169595.4.

*Primary Examiner* — Jack Dinh
(74) *Attorney, Agent, or Firm* — Oblon, McClelland, Maier & Neustadt, L.L.P.

(57) ABSTRACT

An ophthalmologic apparatus includes a refractive power application unit, a storage unit, and a control unit. The refractive power application unit is configured to be capable of changing refractive power applied to a subject's eye. The storage unit stores at least a measurement value of eye refractive power obtained by a measurement performed for the subject's eye in the past. The control unit controls the refractive power application unit to selectively apply the measurement value and one or more refractive values different from the measurement value to the subject's eye in response to the input of an instruction to change refractive power applied to the subject's eye.

19 Claims, 16 Drawing Sheets

(51) Int. Cl.
  *A61B 3/12* (2006.01)
  *A61B 3/16* (2006.01)

(56) References Cited

U.S. PATENT DOCUMENTS

2008/0158509 A1  7/2008  Kubota et al.
2013/0208244 A1  8/2013  Sakagawa

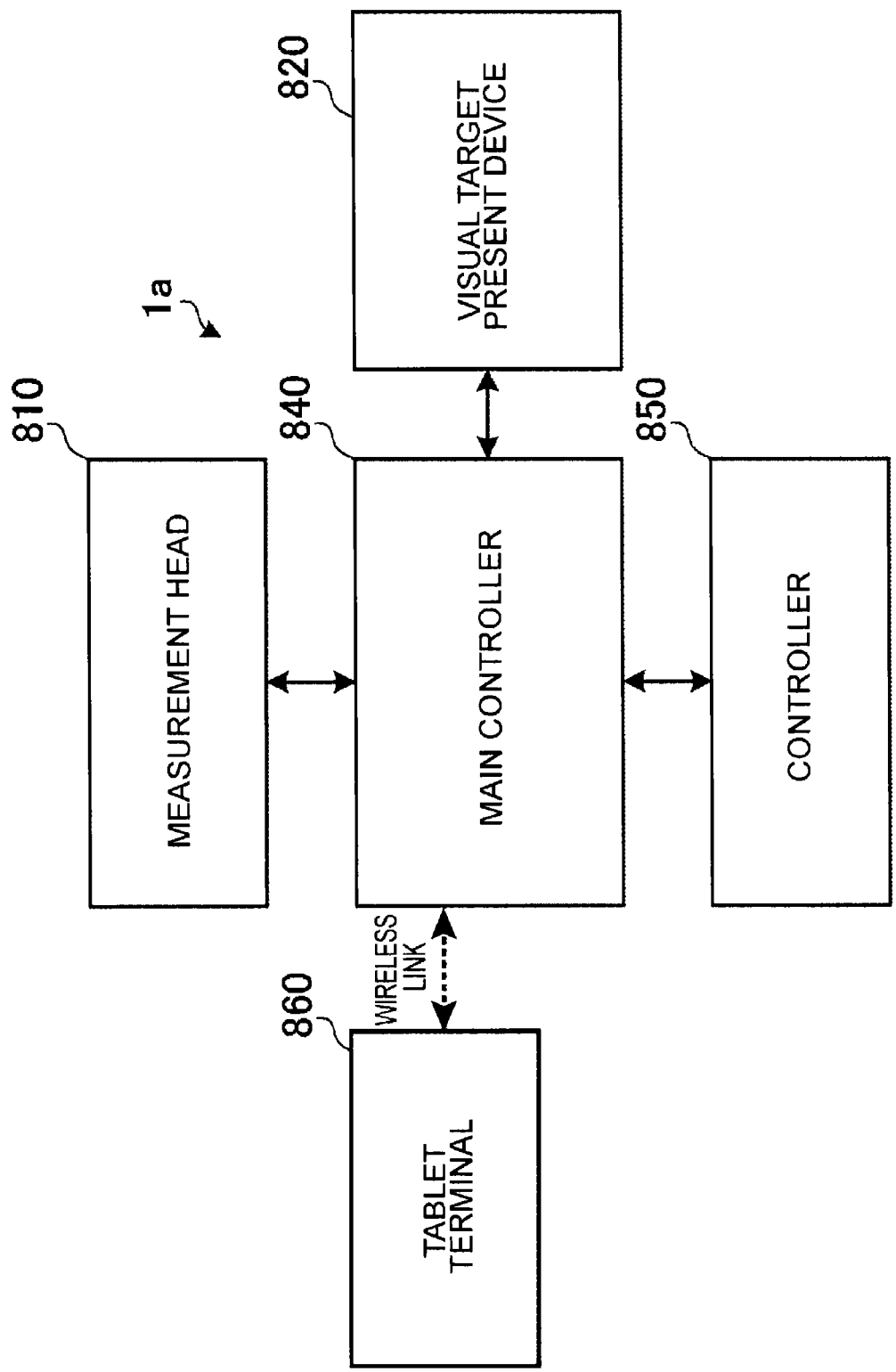

OPHTHALMOLOGIC APPARATUS

CROSS-REFERENCE TO RELATED APPLICATION

This application is based upon and claims the benefit of priority from U.S. Provisional Application No. 62/004,583, filed May 29, 2014; the entire contents of which are incorporated herein by reference.

FIELD

Embodiments described herein relate generally to an ophthalmologic apparatus.

BACKGROUND

An ophthalmologic apparatus is a device that is usable in the ophthalmologic field. In the ophthalmologic field, tests or examinations are classified into objective ones and subjective ones.

Through an objective test, information related to a subject's eye is obtained mainly by a physical method without reference to a response from the subject (see patent documents 1 and 2). The objective test includes an objective measurement for measuring a value related to the subject's eye, imaging for acquiring an image of the subject's eye, and the like. Typical examples of the objective test include objective refractivity measurement, corneal shape measurement, intraocular pressure measurement, fundus photographing, and optical coherence tomography (OCT).

On the other hand, through a subjective test, the result is obtained based on a response from the subject (see patent documents 1 and 2). Typical examples of the subjective test include visual field test and subjective refractivity measurement such as far vision test, near vision test, contrast test, and glare test. In the subjective test, information (visual targets or optotypes, etc.) is presented to a subject, and the result is obtained based on a response to the information from the subject. For example, tests such as a far vision test and a near vision test are conducted using a measurement value obtained by an objective measurement. The far vision test is used to obtain the far visual acuity of the subject's eye and the far sight power of a prescribed lens using optotypes arranged spatially or optically at a first distance (e.g., 5 meters, 6 meters, 20 feet, etc.). The near vision test is used to obtain the near visual acuity of the subject's eye and the near sight power (additional power) of a prescribed lens using optotypes arranged spatially or optically at a second distance (shorter than the first distance, e.g., 30 centimeters, 40 centimeters, etc.). The contrast test is conducted as the contrast of presented visual targets is being changed (or using a stripe visual target, etc.) to obtain the spatial frequency characteristics (contrast sensitivity) of a visual system including the subject's eye. The glare test is applied to the case where opacity occurs in intermediate optic media as in the cataract and corneal clouding, a follow-up after corneal refractive surgery, and the like. The glare test is conducted by presenting a visual target illuminated by a background light (glare light source) to obtain the influence of a reduction in the contrast of a retinal image due to scattering of light caused by an opacity or the like (difficulty with glare).

BRIEF DESCRIPTION OF THE DRAWINGS

FIG. 16 is a schematic block diagram of an ophthalmologic apparatus according to an embodiment.

DETAILED DESCRIPTION

In general, according to one embodiment, an ophthalmologic apparatus includes a refractive power application unit, a storage unit, and a control unit. The refractive power application unit is configured to be capable of changing refractive power applied to a subject's eye. The storage unit stores at least a measurement value of eye refractive power obtained by a measurement performed for the subject's eye in the past. The control unit controls the refractive power application unit to selectively apply the measurement value and one or more refractive values different from the measurement value to the subject's eye in response to the input of an instruction to change refractive power applied to the subject's eye.

First Embodiment

According to a first embodiment, an ophthalmologic apparatus is capable of performing at least one of arbitrary subjective tests and arbitrary objective tests. The ophthalmologic apparatus of the first embodiment is described below as being capable of far vision test, near vision test, contrast test, glare test, and the like as the subjective tests as well as objective refractivity measurement, corneal shape measurement, and the like as the objective tests. However, the ophthalmologic apparatus of the embodiment is not so limited.

(External Structure of the Ophthalmologic Apparatus)

Figure 1:
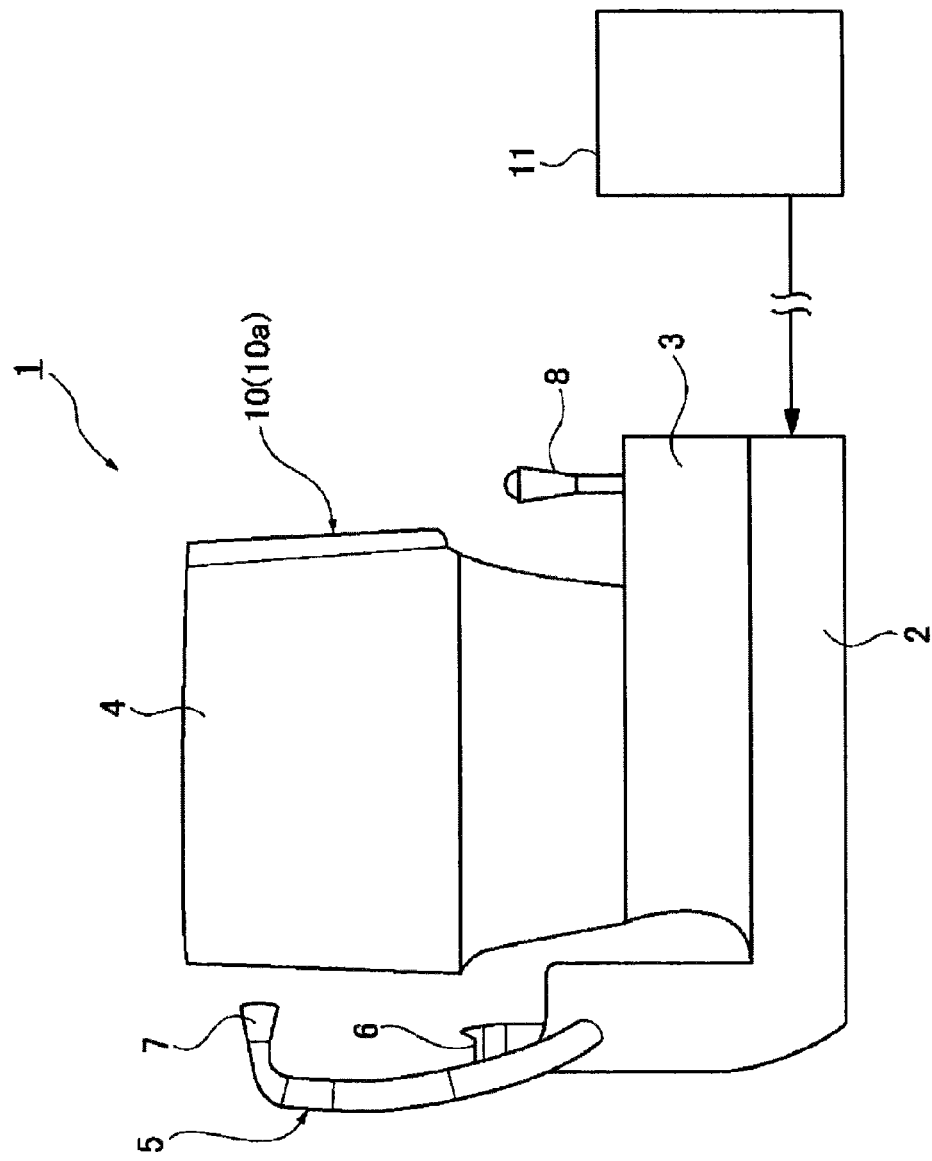
FIG. 1 is a schematic view of an example of an ophthalmologic apparatus according to an embodiment.

FIG. 1 illustrates the external structure of the ophthalmologic apparatus of the first embodiment. An ophthalmologic apparatus 1 includes a base 2, a stage 3, a head 4, a face support 5, a joystick 8, and a display 10. The ophthalmologic apparatus 1 may be a single device or may be constituted of a combination of plural devices. In the latter case, plural constituent elements described below are distributedly arranged in two or more devices. For example, the ophthalmologic apparatus 1 may include a device having an optical system, a drive mechanism, a control circuit board, etc. for conducting tests, and a device for input of instructions and information to the device and output of information from the device.

The stage 3 is movable in front, back, left and right directions with respect to the base 2. The head 4 is formed integrally with the stage 3. The face support 5 is formed integrally with the base 2.

The face support 5 includes a jaw holder 6 and a forehead rest 7. The face support 5 fixes the face of a subject (not illustrated). For example, the examiner is located opposite the subject with respect to the ophthalmologic apparatus 1 while conducting a test. The joystick 8 and the display 10 are provided on the side of the examiner. The joystick 8 is located on the stage 3. The display 10 is located on a surface of the head 4 to face the examiner. The display 10 may be, for example, a flat panel display such as a liquid crystal display (LCD). The display 10 has a touch panel display screen 10a.

The head 4 moves in front, back, left and right directions by pushing and pulling the joystick 8. In addition, the head 4 moves up and down by rotating the joystick 8 about its axis. In response to these operations, the position of the head 4 changes with respect to the face of a subject held by the face support 5. Incidentally, the head 4 is moved left or right to change the test object from the left eye to the right eye or vice versa.

An external device 11 is connected to the ophthalmologic apparatus 1. The external device 11 may be an arbitrary device, and the connection form (communication mode, etc.) between the ophthalmologic apparatus 1 and the external device 11 may also be arbitrary. The external device 11 includes, for example, an eyeglass lens measurement device for measuring the optical properties of lenses. The eyeglass lens measurement device measures the lens power of eyeglasses worn by a subject and the like, and feeds the measurement data to the ophthalmologic apparatus 1. The external device 11 may also be another arbitrary ophthalmologic apparatus. The external device 11 may also be a device (reader) having the function of reading information from a recording medium or a device (writer) having the function of writing information to a recording medium.

Another example of the external device 11 is a computer used in the medical institution. Such in-hospital computer includes, for example, a hospital information system (HIS) server, a Digital Imaging and Communications in Medicine (DICOM) server, and a doctor terminal. The external device 11 may include a computer used outside the medical institution. Examples of such non-hospital computer include mobile terminals, personal terminals, servers and terminals of the maker of the ophthalmologic apparatus 1, and cloud servers.

(Structure of the Optical System)

The ophthalmologic apparatus 1 includes an optical system for testing subjects' eyes. An example of the structure of the optical system is described with reference to FIGS. 2 to 6. The optical system is provided in the head 4. The optical system includes an observation system 12, a fixation target projection system 13, an objective measurement system 14, a subjective measurement system 15, and alignment systems 16 and 17. A processor 9 performs various types of processing.

The observation system 12 has functions to observe the anterior segment of a subject's eye E. The fixation target projection system 13 has functions to provide the subject's eye E with a fixation target. The objective measurement system 14 has functions to conduct objective tests. Specifically, the objective measurement system 14 of this embodiment has the function of projecting a predetermined measurement pattern on the eye fundus Ef of the subject's eye E and the function of detecting an image of the measurement pattern projected on the eye fundus Ef. The subjective measurement system 15 has functions to conduct subjective tests. Specifically, the subjective measurement system 15 of this embodiment has functions to provide the subject's eye E with a visual target. The alignment systems 16 and 17 have functions to position (align) the optical system with the subject's eye E. The alignment system 16 has functions for alignment in a direction along the optical axis of the observation system 12 (back-forth directions). The alignment system 17 has functions for alignment in a direction perpendicular to the optical axis of the observation system 12 (up-down directions and left-right directions).

(Observation System 12)

The observation system 12 includes an objective lens 12a, a dichroic filter 12b, a half mirror 12c, a relay lens 12d, a dichroic filter 12e, an imaging lens 12f, and an imaging device 12g (CCD). The output of the imaging device 12g is input to the processor 9. The processor 9 displays an anterior eye image E' on the display 10 based on a signal fed by the imaging device 12g.

Figure 6:
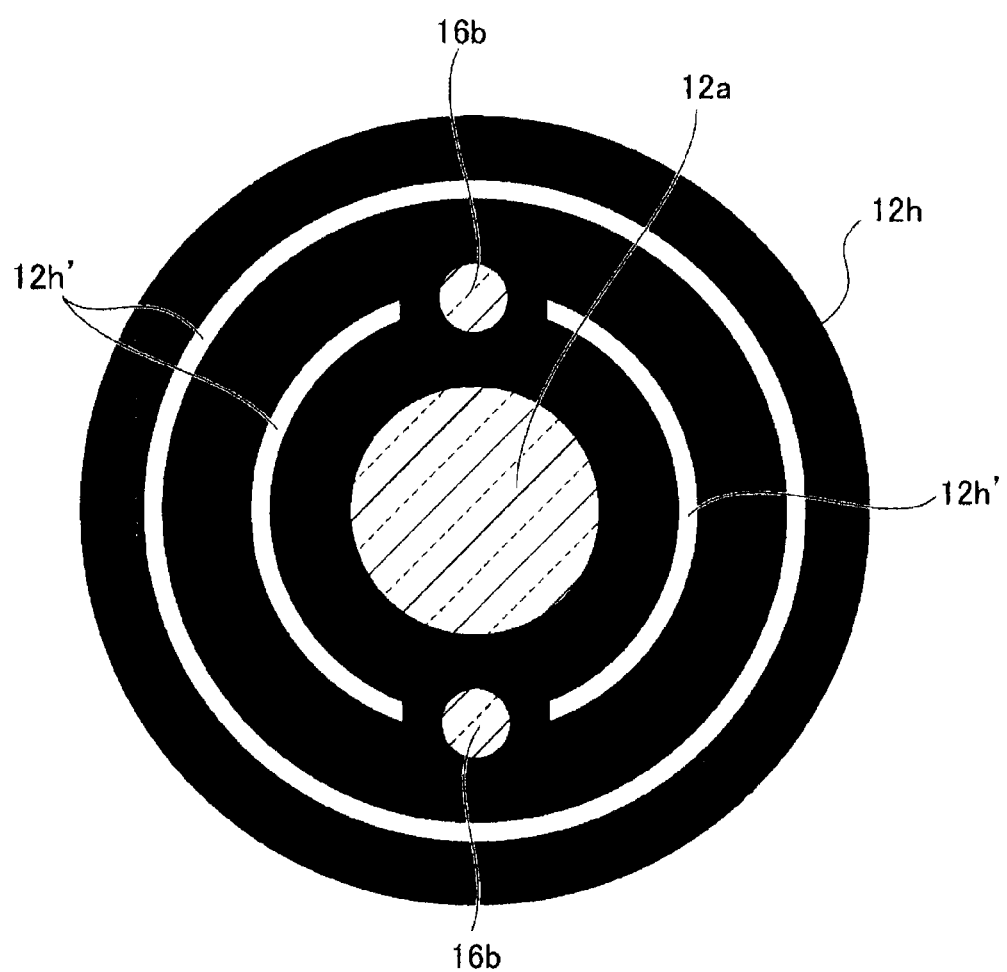
FIG. 6 is a schematic diagram illustrating an example of the structure of the ophthalmologic apparatus of the embodiment.

A kerato-board 12h is provided between the objective lens 12a and the subject's eye E. The kerato-board 12h is used to project an annular (ring-shaped) light flux for measuring the corneal shape on the cornea C of the subject's eye E. FIG. 6 illustrates an example of the structure of the kerato-board 12h.

(Alignment Systems 16 and 17)

The alignment system 16 is located behind the kerato-board 12h. As described above, the alignment system 16 is used for alignment in the back-forth directions. The alignment system 16 includes an alignment light source 16a and a projection lens 16b. The projection lens 16b converts a light flux emitted from the alignment light source 16a into a parallel light flux and projects it on the cornea C. A user or the processor 9 moves the head 4 in the back-forth directions while referring to an image (bright spot image) that the alignment system 16 has projected on the cornea C to achieve alignment.

The alignment system 17 forms an optical path branched from the observation system 12 via the half mirror 12c. As described above, the alignment system 17 is used for alignment in the up-down directions and the left-right directions. The alignment system 17 includes an alignment light source 17a and a projection lens 17b. The projection lens 17b converts a light flux emitted from the alignment light source 17a into a parallel light flux. The parallel light flux is reflected on the half mirror 12c, passes through the optical path of the observation system 12, and is projected on the cornea C. A user or the processor 9 moves the head 4 in the up-down direction and the left-right direction while referring to an image (bright spot image) that the alignment system 17 has projected on the cornea C to achieve alignment.

Figure 2:
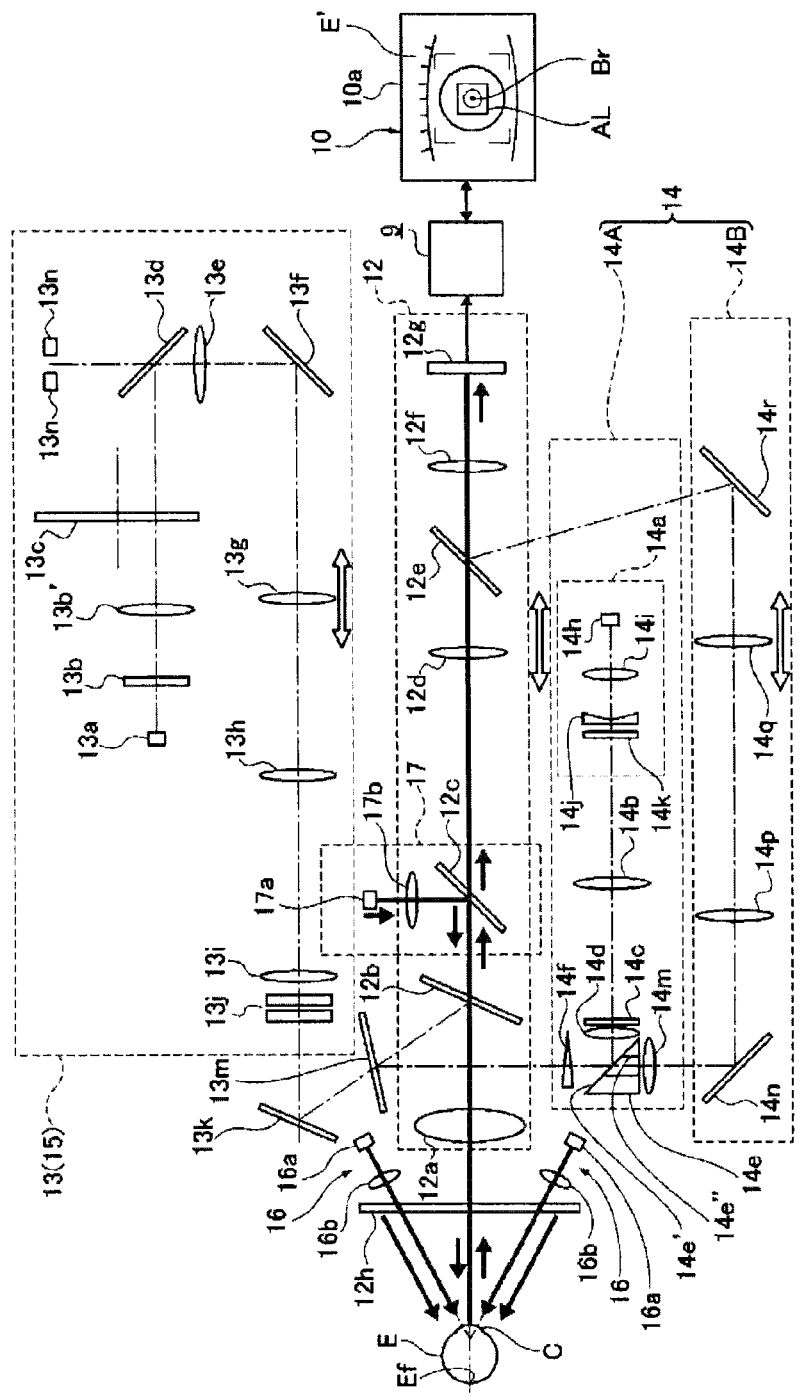
FIG. 2 is a schematic diagram illustrating an example of the structure of the ophthalmologic apparatus of the embodiment.

As illustrated in FIG. 2 and other figures, an alignment mark AL and a bright spot image Br are displayed on the display screen 10a together with the anterior eye image E'. The back-forth alignment is performed by, for example, adjusting the position of the head 4 so that the bright spot image Br formed by the alignment light source 17a comes in focus. Besides, the back-forth alignment may be performed by adjusting the position of the head 4 so that the ratio of the distance between two bright spot images formed by the alignment light source 16a and the diameter of a kerato-ring image is brought within a predetermined range.

To accomplish manual alignment, for example, a user manipulates the joystick 8 while referring to information displayed in the display screen 10a to thereby adjust the position of the head 4. On this occasion, for example, the processor 9 may calculate a misalignment amount from the above ratio, and display it on the display screen 10a. The processor 9 may exert control to start measurement in response to the completion of the alignment.

To accomplish automatic alignment, for example, the processor 9 calculates a misalignment amount from the above ratio, and controls the electric actuation mechanism to move the head 4 so that the misalignment is corrected. This mechanism includes an actuator that generates a driving force and a member that transmits the driving force to the head 4. The processor 9 may exert control so that measurement is started in response to the completion of the alignment.

(Fixation Target Projection System 13, Subjective Measurement System 15)

The fixation target projection system 13 (the subjective measurement system 15) includes an LED light source 13a that emits white light, a color correction filter 13b, a collimator lens 13b', a chart board 13c, a half mirror 13d, a relay lens 13e, a reflective mirror 13f, a focus lens 13g, a relay lens 13h, a field lens 13i, a variable cross-cylinder (VCC) lens 13j, a reflective mirror 13k, dichroic filters 13m and 12b, and the objective lens 12a. The subjective measurement system 15 includes a glare light source 13n that irradiates glare light on the subject's eye E.

The chart board 13c has a fixation target and a visual target chart. The fixation target is used for the visual fixation of the subject's eye E. The fixation target of this embodiment is, for example, a landscape chart. The visual target chart is used to subjectively measure visual acuity and vision correction degree (far sight power, near sight power, etc.) for the subject's eye E. In this embodiment, a plurality of visual target charts is formed in the chart board 13c.

In an objective test (objective refractivity measurement, etc.), the landscape chart is projected on the eye fundus Ef. Alignment is performed while a subject stares at the landscape chart, and the refractive power of the subject's eye E is measured in foggy vision.

(Objective Measurement System 14)

The objective measurement system 14 includes an annular light flux projection system 14A and an annular light flux receiving system 14B. The annular light flux projection system 14A projects an annular measurement pattern on the eye fundus Ef. The annular light flux receiving system 14B detects light of the measurement pattern reflected from the eye fundus Ef.

The annular light flux projection system 14A includes a refractive measurement unit 14a, a relay lens 14b, a pupil aperture 14c, a field lens 14d, a holed prism 14e, a rotary prism 14f, the dichroic filters 13m and 12b, and the objective lens 12a. The refractive measurement unit 14a includes a light source 14h (LED) for refractive measurement, a collimator lens 14i, a conical prism 14j, and an annular measurement pattern formation board 14k.

The annular light flux receiving system 14B includes the objective lens 12a, the dichroic filters 12b and 13m, the rotary prism 14f, the holed prism 14e, the field lens 14d, a reflective mirror 14n, a relay lens 14p, a focus lens 14q, a reflective mirror 14r, the dichroic filter 12e, the imaging lens 12f, and the imaging device 12g (CCD).

Each part of the ophthalmologic apparatus 1 operates under the control of the processor 9. For example, the processor 9 controls the LED light source 13a, the light source 14h, the glare light source 13n, the alignment light sources 16a and 17a, a kerato-ring light source 12h' of the kerato-board 12h, the refractive measurement unit 14a, the focus lenses 13g and 14q, the chart board 13c, the VCC lens 13j, the display 10, and the like.

(Corneal Shape Measurement)

Referring to FIG. 2, the dichroic filter 12b transmits an annular light flux projected on the cornea C for corneal shape measurement and light fluxes from the alignment systems 16 and 17. When the processor 9 outputs these light fluxes, the imaging device 12g obtains the anterior eye image E', a virtual image (not illustrated), and the bright spot image Br.

(Objective Measurement Function)

Figure 3:
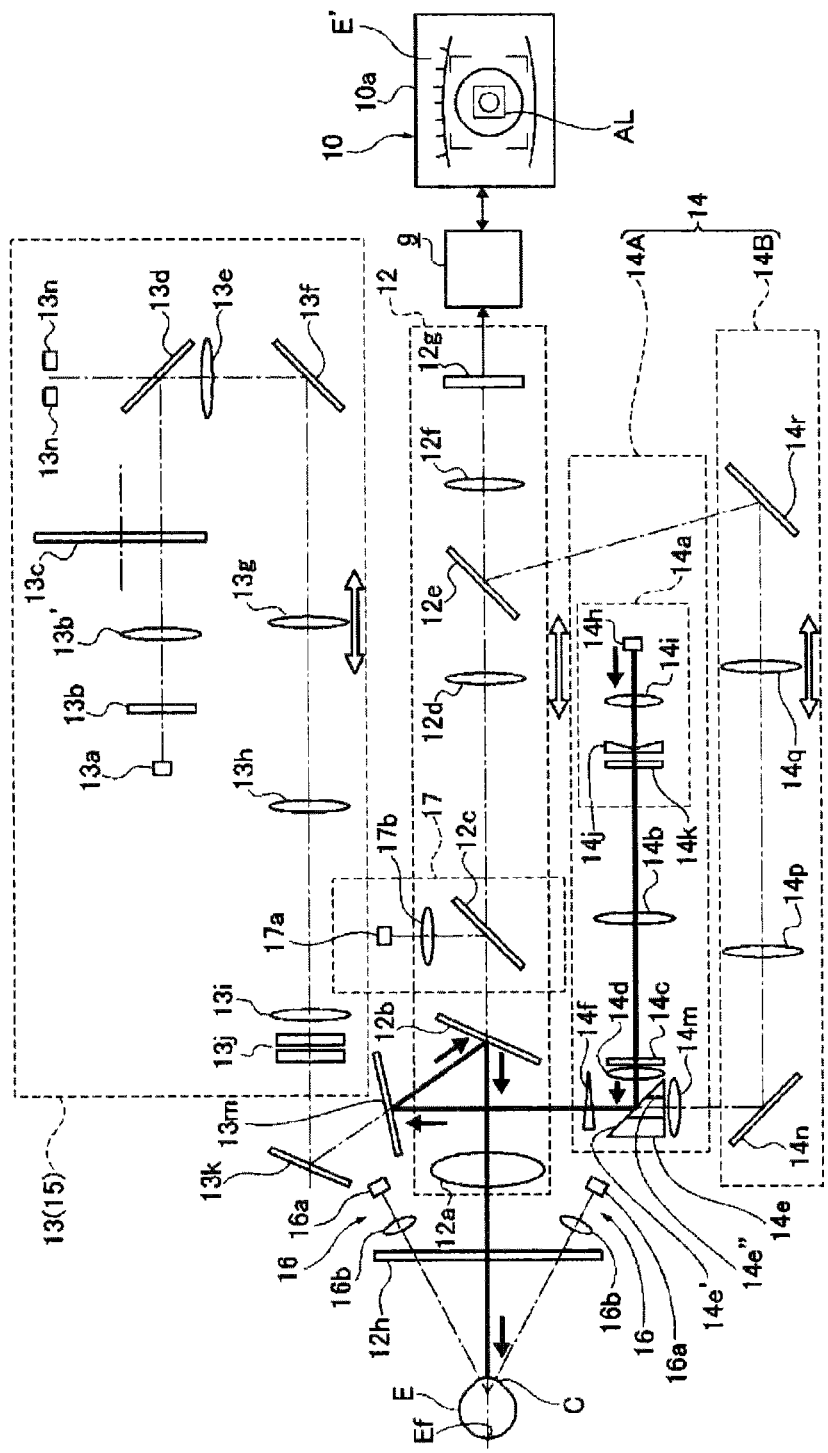
FIG. 3 is a schematic diagram illustrating an example of the structure of the ophthalmologic apparatus of the embodiment.
Figure 4:
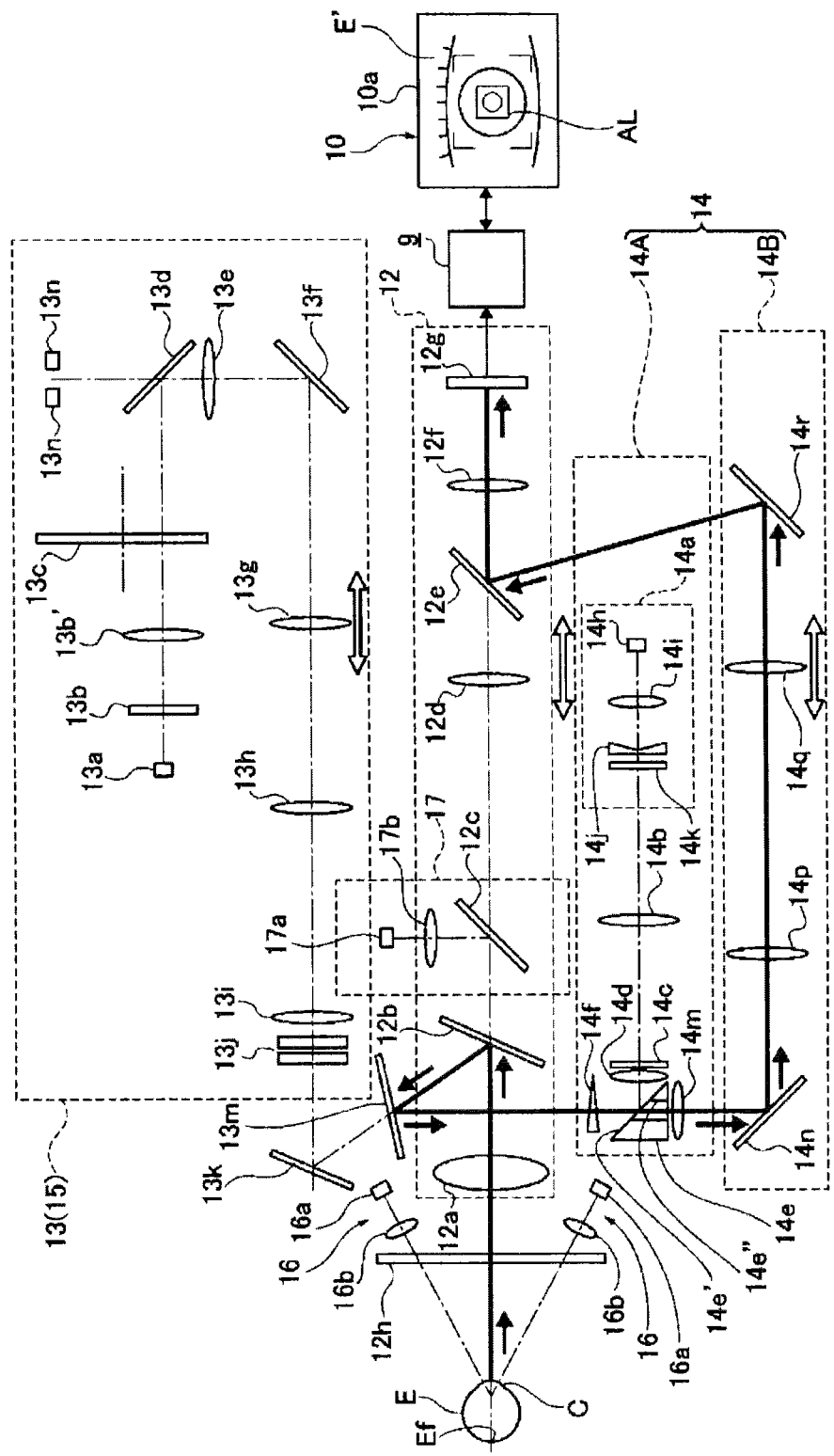
FIG. 4 is a schematic diagram illustrating an example of the structure of the ophthalmologic apparatus of the embodiment.

The following description is referring to FIGS. 3 and 4. When objective measurement mode is selected, the processor 9 turns on the light source 14h. The refractive measurement unit 14a is moved in the optical axis direction and, correspondingly to this, the focus lens 14q is also moved in the optical axis direction.

As illustrated in FIG. 3, the annular measurement pattern (light flux) is led to the dichroic filter 13m via the relay lens 14b, the pupil aperture 14c, the field lens 14d, and a reflective surface 14e' of the holed prism 14e. The measurement pattern reflected on the dichroic filter 13m is led to the objective lens 12a via the dichroic filter 12b and projected on the eye fundus Ef.

As illustrated in FIG. 4, the annular measurement pattern formed on the eye fundus Ef is focused by the objective lens 12a. The measurement pattern travels through the dichroic filters 12b and 13m, the rotary prism 14f, a hole 14e" of the holed prism 14e, a field lens 14m, the reflective mirror 14n, the relay lens 14p, the focus lens 14q, the reflective mirror 14r, and the dichroic filter 12e, and is formed into an image on the imaging device 12g by the imaging lens 12f. Thus, the imaging device 12g detects an image (not illustrated) of the annular measurement pattern.

(Subjective Measurement Function)

Figure 5:
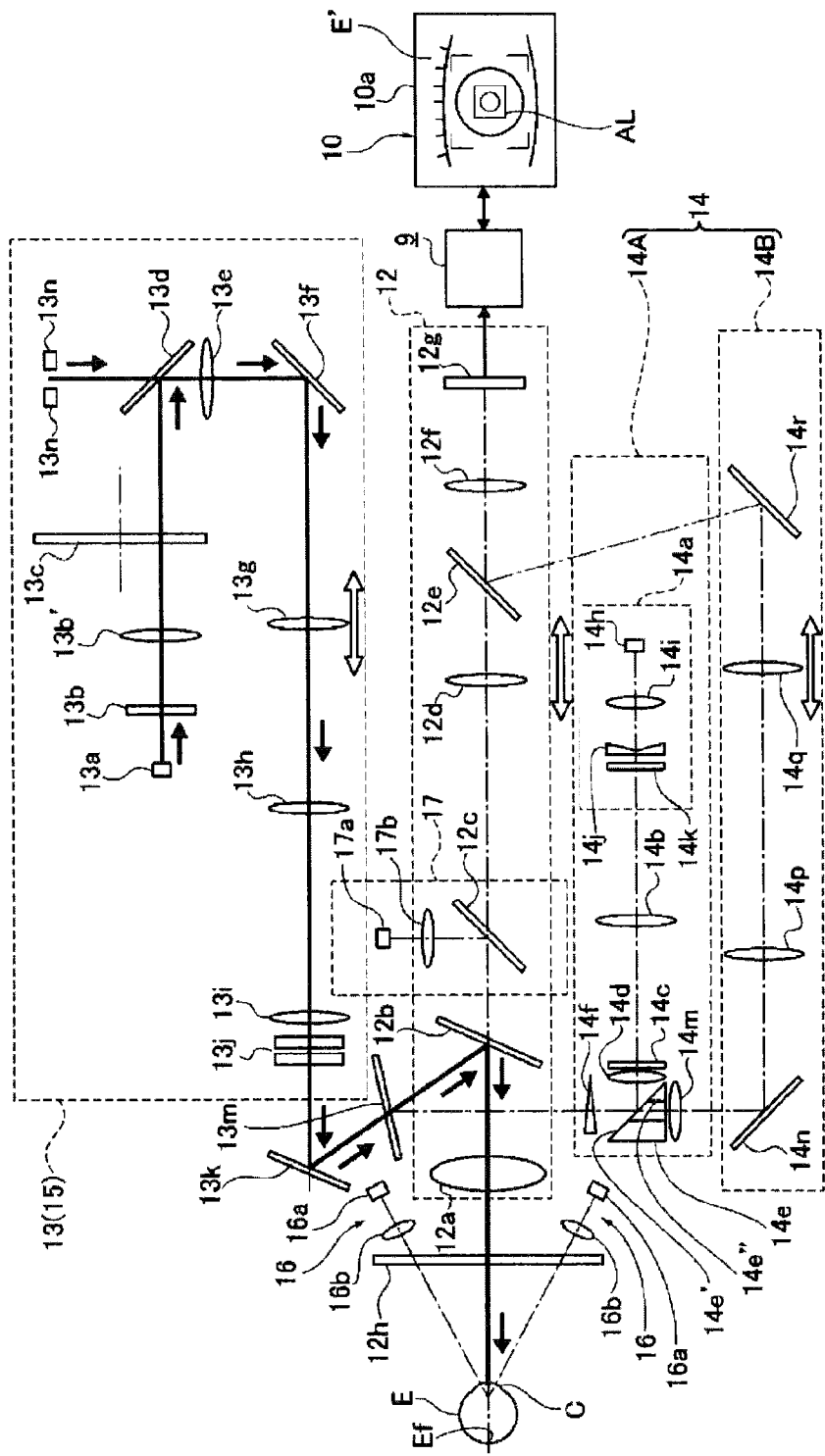
FIG. 5 is a schematic diagram illustrating an example of the structure of the ophthalmologic apparatus of the embodiment.

The following description is referring to FIG. 5. When subjective measurement mode is selected, the processor 9 turns on the LED light source 13a. A light flux emitted from the LED light source 13a illuminates the chart board 13c via the color correction filter 13b. The chart board 13c is provided with a variety of visual targets (charts). The processor 9 moves the focus lens 13g to a position corresponding to the results of an objective measurement. Similarly, the processor 9 controls the VCC lens 13j so that astigmatic vision is corrected based on the astigmatism (degree of astigmatism, astigmatic axis angle) of the subject's eye E obtained by the objective measurement. The degree of astigmatism can be changed by rotating two cylinder lenses that constitute the VCC lens 13j individually in mutually opposite directions. The astigmatic axis angle can be changed by rotating the two cylinder lenses that constitute the VCC lens 13j in the same direction by the same angle.

When the user or the processor 9 selects a visual target, the processor 9 controls the chart board 13c so that the selected visual target is arranged in the optical path. The light flux passes through the visual target and travels through the half mirror 13d, the relay lens 13e, the reflective mirror 13f, the focus lens 13g, the relay lens 13h, the field lens 13i, the VCC lens 13j, the dichroic filters 13m and 12b, and the objective lens 12a. The light flux is then projected on the eye fundus Ef.

The subject submits a response with respect to the visual target projected on the eye fundus Ef. The selection of a visual target and response to the visual target are repeated according to the judgment of the user or the processor 9. The user or the processor 9 determines a prescription based on the response from the subject.

For example, to determine a prescription, the processor 9 first moves the focus lens 13g to a reference position corresponding to the result of the objective measurement. In addition, the processor 9 rotates the two cylinder lenses that constitute the VCC lens 13j to rotation angles corresponding to the result of the objective measurement. When the position of the focus lens 13g is determined based on a response from the subject, the processor 9 finds a correction amount for the spherical power according to the amount of movement of the focus lens 13g using the above reference position as a reference. The processor 9 corrects the spherical power obtained by the objective measurement based on the correction amount to thereby obtain a new spherical power. Next, a visual target chart is presented to the subject to measure the astigmatic axis angle. When the rotation angle of the VCC lens 13j is determined based on a response to the visual target chart from the subject, the processor 9 corrects the astigmatic axis angle by the determined rotation angle. A cross-cylinder chart is presented to the subject to measure the degree of astigmatism. When the rotation angles of the two cylinder lenses that constitute the VCC lens 13j are determined based on a response to the cross-cylinder chart from the subject, the processor 9 corrects the degree of astigmatism by the determined rotation angles of the two cylinder lenses. Further, a red-green chart is presented to the subject to measure a balance between the two eyes. When the position of the focus lens 13g is determined based on a response to the red/green chart from the subject, the processor 9 finds again a correction amount for the spherical power according to the amount of movement of the focus lens 13g using the above reference position as a reference. The processor 9 corrects the spherical power in the same manner as described above to obtain a new spherical power. As described above, the processor 9 determines the spherical power, degree of astigmatism, and astigmatic axis angle for the subjective test based on the responses from the subject.

When a glare test is conducted, the processor 9 turns on the glare light source 13n. Then, a subjective measurement is performed in this state.

Regarding the structure of the objective measurement system 14, the subjective measurement system 15, the alignment systems 16 and 17, and the kerato-system, and the principles of eye refractive power measurement, subjective measurement, and corneal shape measurement, they are generally known, and therefore the detailed description is not provided herein.

(Structure of Information Processing System)

Figure 7:
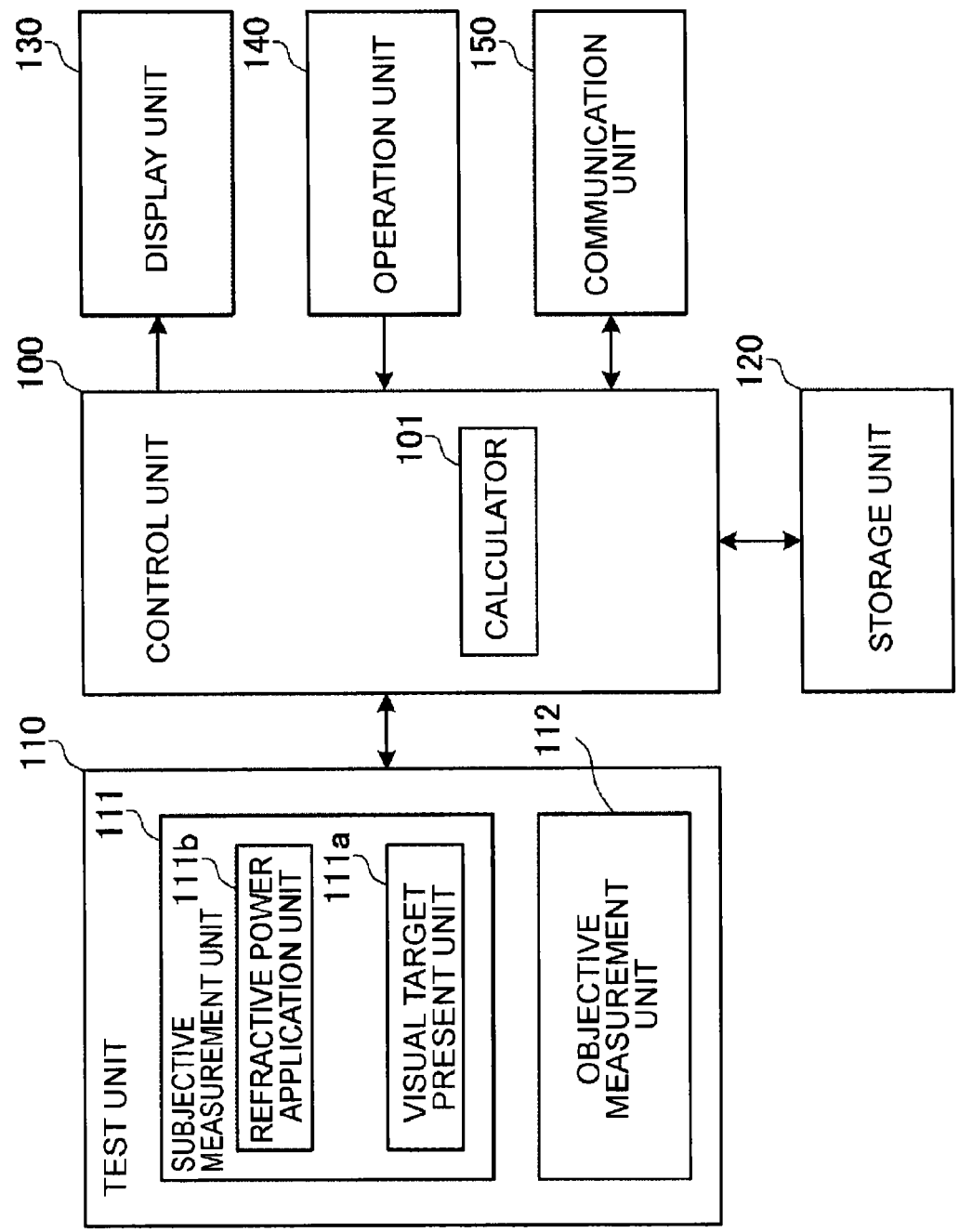
FIG. 7 is a schematic block diagram of the ophthalmologic apparatus of the embodiment.

Described below is the information processing system of the ophthalmologic apparatus 1. FIG. 7 illustrates an example of the functional structure of the information processing system of the ophthalmologic apparatus 1. The information processing system includes a control unit 100, a test unit 110, a storage unit 120, a display unit 130, an operation unit 140, and a communication unit 150. The control unit 100 controls the test unit 110, the display unit 130, and the communication unit 150.

(Test Unit 110)

The test unit 110 is capable of different types of tests. Examples of variety of tests that can be conducted with the ophthalmologic apparatus 1 having a structure as illustrated in FIG. 2 include objective refractivity measurement, subjective refractivity measurement (far vision test, near vision test, contrast test, glare test, etc.), corneal shape measurement, and the like. The test unit 110 includes a subjective measurement unit 111 and an objective measurement unit 112. The subjective measurement unit 111 performs subjective measurement for the subject's eye E and thereby obtains a measurement value (subjective measurement value). The subjective measurement unit 111 includes a visual target present unit 111a and a refractive power application unit 111b. The visual target present unit 111a presents a visual target corresponding to the type of subjective refractivity measurement to the subject's eye E. The refractive power application unit 111b applies a variable refractive power to the subject's eye E. The objective measurement unit 112 performs objective measurement for the subject's eye E and thereby obtains a measurement value (objective measurement value).

The test unit 110 includes the optical system illustrated in, for example, FIG. 2 and a mechanism for driving each unit/member. The test unit 110 may include functions for obtaining test results by analyzing data acquired by the optical system. In this case, the test unit 110 includes at least part of the processor 9 as illustrated in FIG. 2.

(Storage Unit 120)

The storage unit 120 stores various computer programs and data. The computer programs include a control program and an operation program for performing various tests on the ophthalmologic apparatus 1. The control unit 100 includes a central processing unit (CPU). The CPU loads the computer programs stored in the storage unit 120 and executes them so that the ophthalmologic apparatus 1 performs various tests. The data includes measurement values of the refractive power of the subject's eye E obtained by measurements in the past. The past measurements include objective measurements and subjective measurements conducted in the past. In this embodiment, the storage unit 120 stores at least measurement values (objective measurement values, subjective measurement values) obtained by measurements performed in the past. The storage unit 120 may store one or more refractive values different from the measurement values.

(Display Unit 130, Operation Unit 140)

The display unit 130 displays information under the control of the control unit 100. The display unit 130 includes the display 10 as illustrated in FIG. 1.

The operation unit 140 is used to operate the ophthalmologic apparatus 1. The operation unit 140 includes various types of hardware keys (the joystick 8, buttons, switches, etc.). The operation unit 140 further includes various types of software keys (buttons, icons, menus, etc.) displayed on the touch-panel display screen 10a.

The display unit 130 and the operation unit 140 may be at least partially integrated. A typical example of this is the touch-panel display screen 10a.

(Communication Unit 150)

The communication unit 150 has the function of communicating with the external device 11 illustrated in FIG. 1. The communication unit 150 may be provided to, for example, the processor 9. The communication unit 150 has a structure corresponding to the mode of communication with the external device 11.

(Control Unit 100)

The control unit 100 is the main constituent element of the information processing system. The control unit 100 performs various types of information processing such as arithmetic processing and control processing. The control unit 100 includes at least part of the processor 9 as illustrated in FIG. 2.

In this embodiment, in response to the input of an instruction to change refractive power applied to the subject's eye E, the control unit 100 controls the refractive power application unit 111b to selectively apply a measurement value and one or more refractive values different from the measurement value to the subject's eye. The one or more refractive values may include a calculation value obtained based on the measurement value. In this case, the control unit 100 includes a calculator 101. Incidentally, at least part of the one or more refractive values may be acquired from the outside. If all of the one or more refractive values are acquired from the outside, the calculator 101 is not necessary.

Each time operation is performed on a single operation unit to instruct the change of refractive power applied to the subject's eye E, the control unit 100 may control the refractive power application unit 111b to sequentially apply the measurement value and the one or more refractive values to the subject's eye E. The order in which the measurement value and the one or more refractive values are to be applied to the subject's eye E is determined in advance. The order can be changed afterwards. Further, each time operation is performed on the single operation unit to instruct the change of refractive power applied to the subject's eye E, the control unit 100 may control the refractive power application unit 111b to cyclically apply the measurement value and the one or more refractive values to the subject's eye E.

(Calculator 101)

The calculator 101 calculates one or more calculation values based on measurement values (objective measurement values or subjective measurement values) obtained by measurements (objective measurements or subjective measurements) performed in the past. The one or more calculation values obtained by the calculator 101 are stored in the storage unit 120. In this embodiment, the measurement values include spherical power, degree of astigmatism, and astigmatic axis angle, and the one or more calculation values obtained by the calculator 101 include equivalent spherical power of the subject's eye E. The calculator 101 calculates the equivalent spherical power SE of the subject's eye E using the following formula (1):

$$SE=S+(C/2) \quad (1)$$

where S is the spherical power of the subject's eye E, and C is the degree of astigmatism.

If one calculation value is obtained based on the measurement values, the control unit 100 controls the refractive power application unit 111b to sequentially or cyclically (i.e., alternately) apply the measurement value and the calculation value obtained by formula (1) based on this measurement value to the subject's eye E each time operation is performed on the single operation unit to instruct the change of refractive power applied to the subject's eye E.

If a measurement value is used as a prescription value, the subject wears a refractive correction (glasses, contact lens, intraocular lens (IOL), etc.) having spherical power, degree of astigmatism, and astigmatic axis angle as correction parameters. On the other hand, if a calculation value is used as a prescription value, the subject wears a refractive correction having equivalent spherical power as a correction parameter (i.e., without degree of astigmatism and astigmatic axis angle as correction parameters). However, the former refractive correction (toric IOL, etc.) is generally more expensive than the latter one (IOL, etc.). Therefore, the subject may wish to determine which one is to be selected in consideration of actual view and the cost.

In this embodiment, in response to the input of an instruction to change refractive power applied to the subject's eye E, a measurement value and a refractive value (calculation value) different from the measurement value are cyclically applied to the subject's eye E. With this, the subject can select a refractive correction by actually checking a difference in vision depending on the refractive power applied to the subject's eye E (Usage)

Described below is the usage of the ophthalmologic apparatus 1 of the embodiment. As described above, the ophthalmologic apparatus 1 is capable of testing the left and right eyes of the subject individually.

Figure 8:
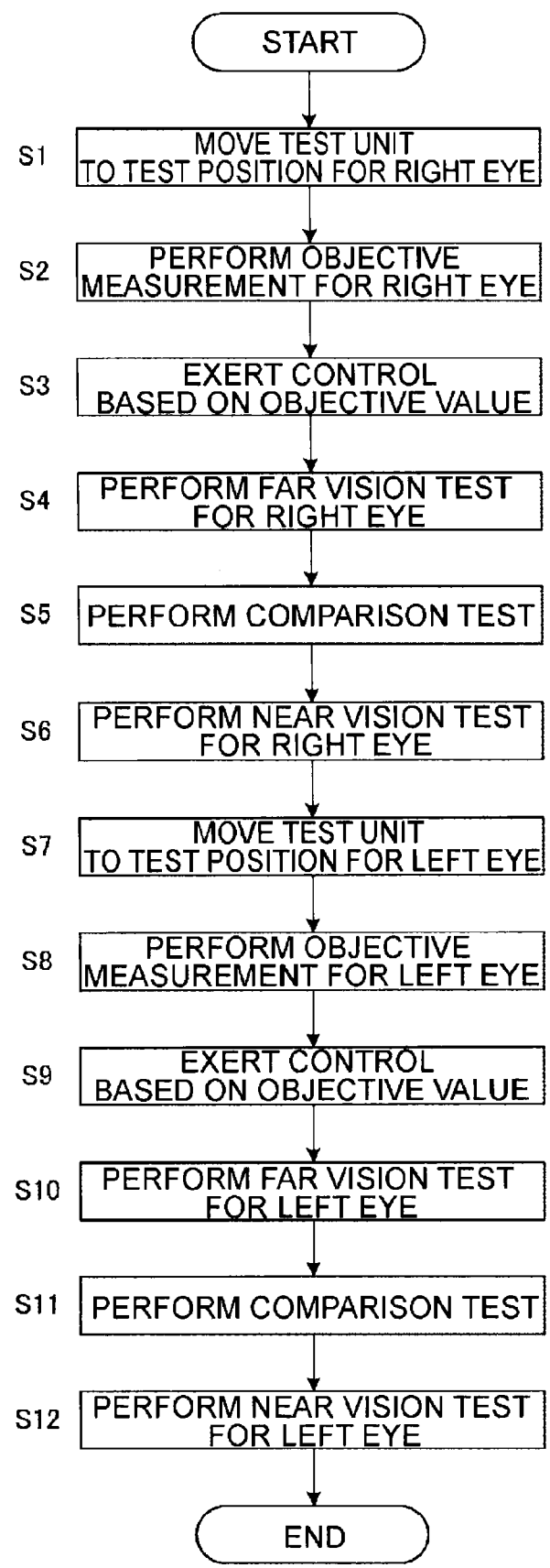
FIG. 8 is a flowchart of an example of the operation of the ophthalmologic apparatus of the embodiment.

FIG. 8 is a flowchart of an example of a test performed by the ophthalmologic apparatus 1 of the embodiment. In this example, objective measurement (objective refractivity measurement) and subjective measurement (subjective refractivity measurement) are performed in this order for the right eye, and then objective measurement and subjective measurement are performed in this order for the left eye. In the subjective measurement, a far vision test and a near vision test are conducted in this order.

(S1)

After the face of the subject is fixed by the face support 5, the test unit 110 (the head 4) is moved to a test position for the right eye. The term "test position" as used herein refers to a position where the subject's eye can be tested. The subject's eye is placed in the test position through the alignment as described above. The test unit 110 is moved by the control unit 100 according to operation or instruction from a user, or instruction by the control unit 100. That is, the test unit 110 is moved to the test position for the right eye and a preparation is made for objective refractivity measurement.

(S2)

After the test unit 110 is situated in the test position for the right eye, objective measurement is performed for the right eye. An objective value (measurement value) obtained by the objective measurement for the right eye is stored in the storage unit 120 by the control unit 100.

(S3)

The control unit 100 exerts control based on the objective value for the right eye obtained in step S2. The control includes, for example, the process of selecting a visual target to be presented first in subjective refractivity measurement (far vision test, near vision test) sequentially performed thereafter.

(S4)

According to an instruction from the user or the control unit 100, the test unit 110 selectively presents various visual targets to the right eye. The user or the ophthalmologic apparatus 1 obtains a far visual acuity (and/or the far sight power of a prescribed lens, the same applies hereinafter) of the right eye based on the responses of the subject to the presented visual targets. The control unit 100 stores the far visual acuity in the storage unit 120.

(S5)

Subsequently, the control unit 100 controls the refractive power application unit 111*b* to cyclically (i.e., alternately) apply the measurement value obtained by the objective measurement in step S2 or the subjective measurement (far vision test) in step S4 and a calculation value obtained based on the measurement value to the right eye. This allows the subject to check differences in visions with respect to the measurement value (spherical power, degree of astigmatism, and astigmatic axis angle) obtained by the objective measurement in step S2 or the subjective measurement in step S4 and the calculation value (equivalent spherical power) based on the measurement value. The subject selects desired one of the calculation value and the measurement value applied to the right eye in step S5, and the control unit 100 stores the desired value in the storage unit 120 as a far visual acuity (prescription value) of the right eye. An example of the control of the control unit 100 in step S5 is described later (see FIG. 9, etc.).

(S6)

After the completion of the comparison test for the right eye, a near vision test is performed for the right eye. The control unit 100 controls the test unit 110 to prepare for the near vision test. According to an instruction from the user or the control unit 100, the test unit 110 selectively presents various visual targets to the right eye. The user or the ophthalmologic apparatus 1 finds a near visual acuity (and/or the near sight power of a prescribed lens, the same applies hereinafter) of the right eye based on the responses of the subject to the presented visual targets. The control unit 100 stores the near visual acuity in the storage unit 120.

(S7)

After completion of the near vision test for the right eye, the test unit 110 is moved to a test position for the left eye.

(S8)

After the test unit 110 is situated in the test position for the left eye, objective measurement is performed for the left eye. An objective value (measurement value) obtained by the objective measurement for the left eye is stored in the storage unit 120.

(S9)

As in step S3, the control unit 100 exerts control based on the objective value for the left eye obtained in step S8. The control includes, for example, the process of selecting a visual target to be presented first in subjective refractivity measurement (far vision test, near vision test) sequentially performed thereafter.

(S10)

A far vision test is performed for the left eye in the same manner as that for the right eye. A far visual acuity obtained by the test is stored in the storage unit 120.

(S11)

Subsequently, the control unit 100 controls the refractive power application unit 111*b* to cyclically apply the measurement value obtained by the objective measurement in step S8 or the subjective measurement (far vision test) in step S10 and a calculation value obtained based on the measurement value to the left eye. This allows the subject to check differences in visions with respect to the measurement value (spherical power, degree of astigmatism, and astigmatic axis angle) obtained by the objective measurement in step S8 or the subjective measurement in step S10 and the calculation value (equivalent spherical power) obtained based on the measurement value. The subject selects desired one of the calculation value and the measurement value applied to the left eye in step S8, and the control unit 100 stores the desired value in the storage unit 120 as a far visual acuity (prescription value) of the left eye. In step 11, the control unit 100 operates in a similar manner as in step S5.

(S12)

After the completion of the comparison test for the left eye, a near vision test is performed for the left eye in the same manner as that for right eye. A near visual acuity obtained by the test is stored in the storage unit 120. Thus, this process ends.

With reference to FIG. 8, an example is described in which the comparison test is performed based on the far visual acuity. Instead of or in addition to this, a comparison test may be performed based on the near visual acuity after the near vision test in step S6 or S12. With this, the vision where the near visual acuity (spherical power, degree of astigmatism, and astigmatic axis angle) obtained by the near vision test is applied can be compared with the vision where the calculation value (equivalent spherical power) obtained from the near visual acuity is applied.

Further, a contrast test and/or a glare test may be performed in arbitrary timing in the flowchart of FIG. 8.

It is assumed, for example, that the user inputs an instruction to conduct a contrast test for the right eye after the completion of the near vision test for the right eye (S6). Upon receipt of the instruction, the control unit 100 prepares for the contrast test. Accordingly, the contrast test is performed for the right eye. A contrast visual acuity obtained by the test is stored in the storage unit 120.

In addition, it is assumed that the user inputs an instruction for a glare test for the right eye after the completion of the contrast test. Upon receipt of the instruction, the control unit 100 prepares for the glare test. This preparation includes the control based on the objective value for the right eye. The control unit 100 may acquire medical information for the right eye (information about the magnitude of cataract, etc.) from an electronic health record, and display the information on the display unit 130. After the preparation, the glare test is performed for the right eye, and the test result is stored in the storage unit 120.

Similarly, it is assumed that the user inputs an instruction to conduct a contrast test for the left eye after the completion of the near vision test for the right eye (S12). Upon receipt of the instruction, the control unit 100 moves the test unit 110 to the test position for the left eye. The control unit 100 provides a preparation, such as the control based on the objective value for the right eye, for the test (contrast test) to be performed next for the left eye. Accordingly, the contrast test is performed for the left eye. A contrast visual acuity obtained by the test is stored in the storage unit 120.

In addition, it is assumed that the user inputs an instruction to conduct a glare test for the left eye after the completion of the contrast test. Upon receipt of the instruction, the control unit 100 prepares for the glare test. This preparation includes the control based on the objective value for the left eye. The control unit 100 may acquire medical information for the left eye (information about the magnitude of cataract, etc.) from an electronic health record, and display the information on the display unit 130. After the preparation, the glare test is performed for the left eye, and the test result is stored in the storage unit 120.

Figure 9:
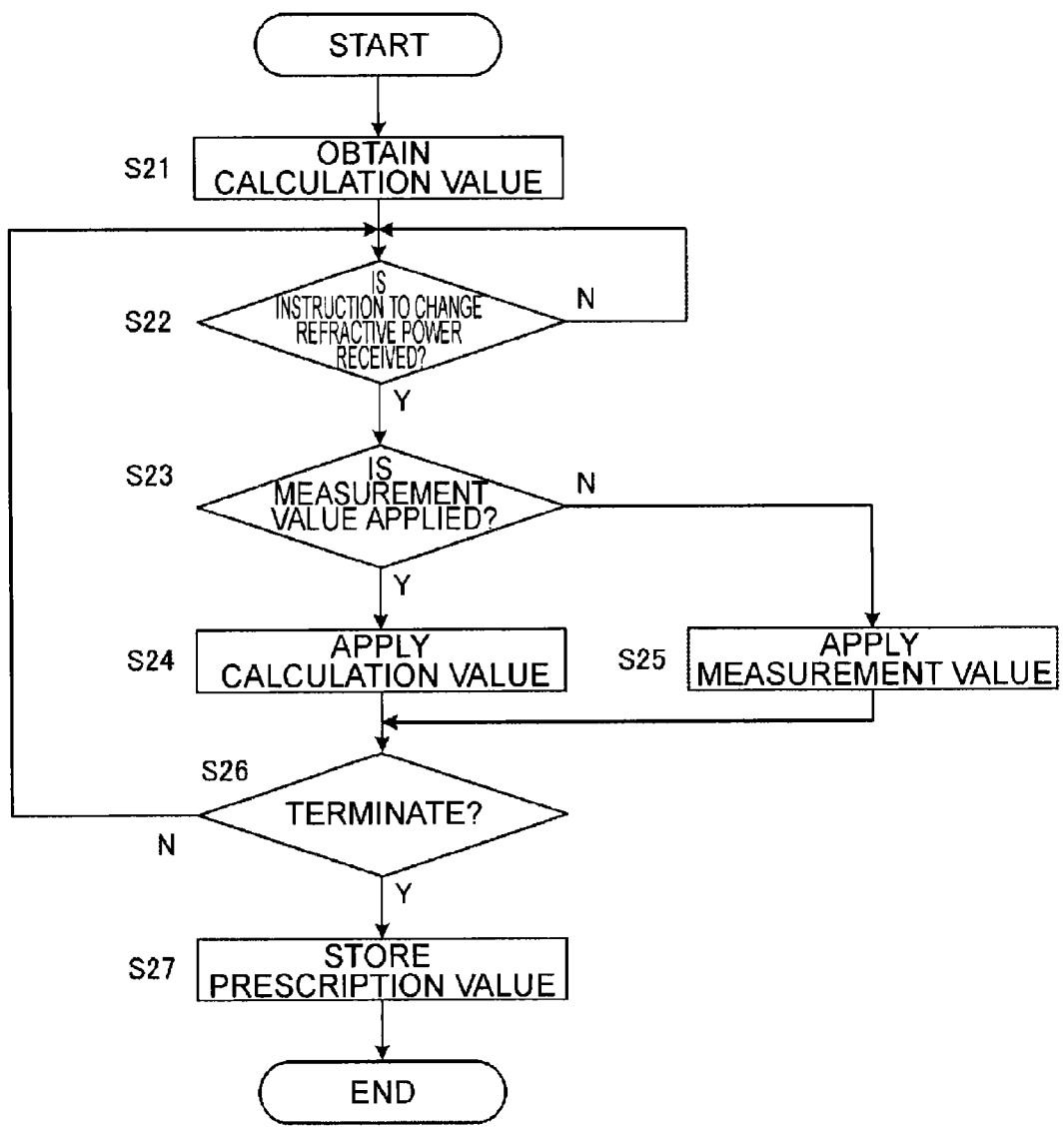
FIG. 9 is a flowchart of an example of the operation of the ophthalmologic apparatus of the embodiment.

FIG. 9 is a detailed flowchart of the comparison test performed in step S5 in FIG. 8. The comparison test in step S11 of FIG. 8 is performed in a similar manner. FIG. 9 illustrates an example in which the control unit 100 controls the refractive power application unit 111*b* to cyclically apply the measurement value and a calculation value obtained based on the measurement value to the right eye.

(S21)

In step S5 in FIG. 8, the calculator 101 obtains a calculation value based on the measurement value obtained by the objective measurement in step S2 or the subjective measurement in step S4. In this embodiment, the calculator 101 obtains equivalent spherical power as a calculation value from spherical power and degree of astigmatism obtained in step S2 or S4 using formula (1). The control unit 100 stores the calculation value obtained by the calculator 101 in the storage unit 120. The timing of this calculation is not necessarily in immediately before step S22. The calculation may be performed in arbitrary timing before step S24 described below.

(S22)

The control unit 100 waits for an instruction from the user to change refractive power through the operation unit 140 (N in S22). Upon receipt of an instruction from the user to change refractive power through the operation unit 140 (Y in S22), the process control of the control unit 100 moves to step S23.

(S23)

Upon receipt of an instruction from the user to change refractive power through the operation unit 140 (Y in S22), the control unit 100 determines whether the measurement value obtained by the objective measurement in step S2 or the subjective measurement in step S4 is applied to the right eye. If the measurement value is applied to the right eye (Y in S23), the process control of the control unit 100 moves to step S24. If not (N in S23), the process control moves to step S25.

(S24)

Having determined that the measurement value is applied to the right eye (Y in S23), the control unit 100 controls the refractive power application unit 111b to apply the calculation value obtained in step S21 to the right eye. Then, the process control of the control unit 100 moves to step S26.

(S25)

Having determined that the measurement value is not applied to the right eye (N in S23), the control unit 100 determines that the calculation value obtained in step S21 is applied to the right eye. The control unit 100 controls the refractive power application unit 111b to apply the measurement value obtained in step S2 or S4 to the right eye. The process control of the control unit 100 moves to step S26.

(S26)

For example, based on an instruction from the user received through the operation unit 140, the control unit 100 determines whether to terminate the comparison test. If the control unit 100 determines to terminate the comparison test (Y in S26), the process control of the control unit 100 moves to step S27. If not (N in S26), the process control of the control unit 100 loops back to step S22.

(S27)

Having determined to terminate the comparison test (Y in S26), the control unit 100 determines the measurement value or the calculation value selected by the subject as a prescription value for the right eye. The control unit 100 stores the prescription value for the right eye in the storage unit 120. With this, the process control for the comparison test ends (End).

Figure 10:
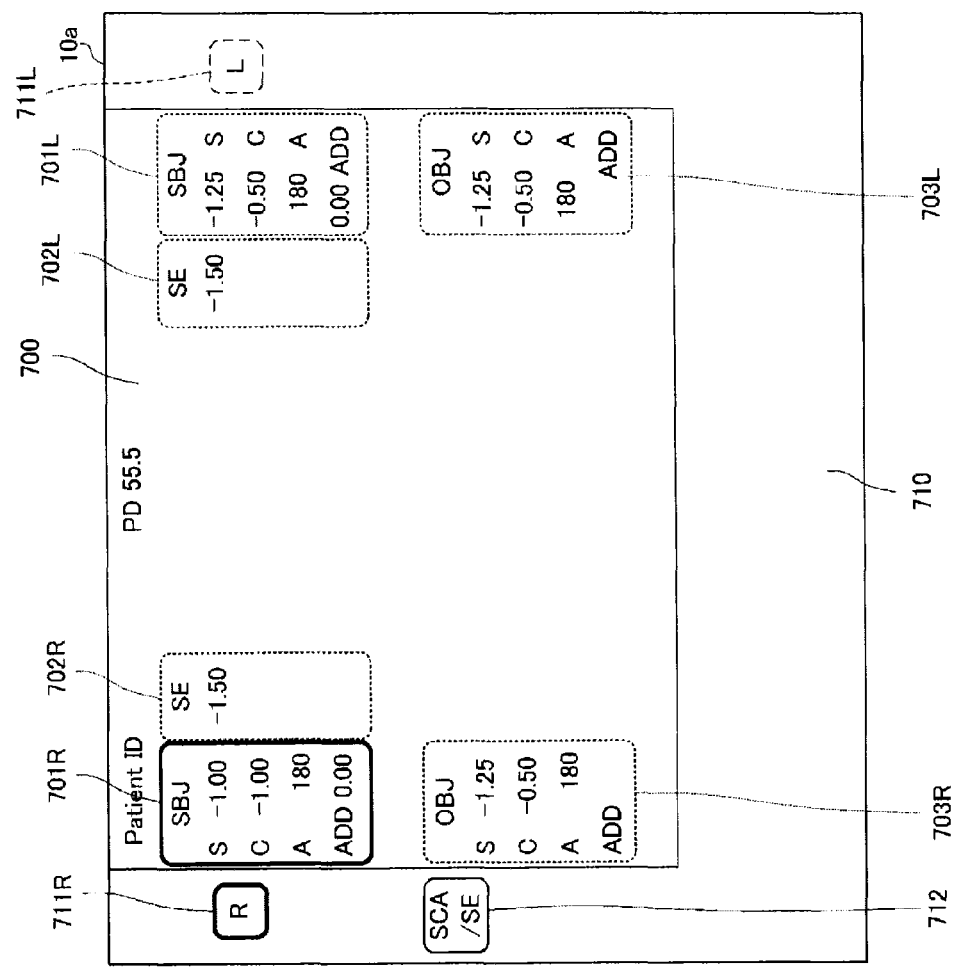
FIG. 10 is a schematic diagram for explaining an example of the operation of the ophthalmologic apparatus of the embodiment.
Figure 11:
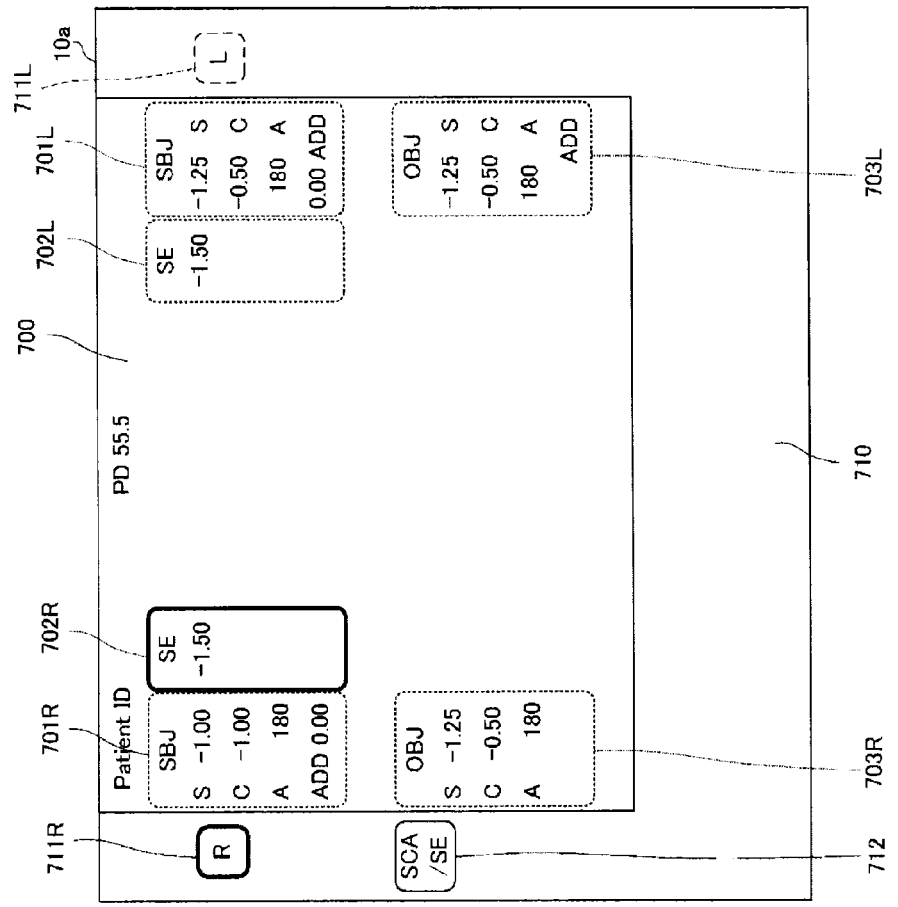
FIG. 11 is a schematic diagram for explaining an example of the operation of the ophthalmologic apparatus of the embodiment.

FIGS. 10 and 11 each illustrate an example of the display screen 10a in the comparison test in step S5. FIG. 10 illustrates an example of the display screen 10a when the measurement value is applied to the right eye. FIG. 11 illustrates an example of the display screen 10a when the calculation value is applied to the right eye. Like reference numerals refer to like parts in FIGS. 10 and 11, and the same description is not repeated.

The display screen 10a, on which various software keys are arranged as the operation unit 140, has a display region 700 and an operation region 710.

The display region 700 contains a right-eye subjective measurement value display region 701R, a right-eye calculation value display region 702R, a right-eye objective measurement value display region 703R, a left-eye subjective measurement value display region 701L, a left-eye calculation value display region 702L, and a left-eye objective measurement value display region 703L. The control unit 100 displays appropriate information in each display region.

The right-eye subjective measurement value display region 701R displays a measurement value obtained by a subjective measurement for the right eye. The right-eye calculation value display region 702R displays a calculation value obtained from the measurement value of the right eye and the type of the calculation value. The right-eye objective measurement value display region 703R displays a measurement value obtained by an objective measurement for the right eye. During subjective measurement for the right eye, the right-eye subjective measurement value display region 701R is displayed with, but readily distinguishable from other display regions. During objective measurement for the right eye, the right-eye objective measurement value display region 703R is displayed with, but readily distinguishable from other display regions. When a measurement value is applied to the right eye during a comparison test for the right eye, the right-eye subjective measurement value display region 701R is displayed with, but readily distinguishable from other display regions. On the other hand, when a calculation value is applied to the right eye during a comparison test for the right eye, the right-eye calculation value display region 702R is displayed with, but readily distinguishable from other display regions.

The left-eye subjective measurement value display region 701L displays a measurement value obtained by a subjective measurement for the left eye. The left-eye calculation value display region 702L displays a calculation value obtained from the measurement value of the left eye and the type of the calculation value. The left-eye objective measurement value display region 703L displays a measurement value obtained by an objective measurement for the left eye. During subjective measurement for the left eye, the left-eye subjective measurement value display region 701L is displayed with, but readily distinguishable from other display regions. During objective measurement for the left eye, the left-eye objective measurement value display region 703L is displayed with, but readily distinguishable from other display regions. When a measurement value is applied to the left eye during a comparison test for the left eye, the left-eye subjective measurement value display region 701L is displayed with, but readily distinguishable from other display regions. On the other hand, when a calculation value is applied to the left eye during a comparison test for the left eye, the left-eye calculation value display region 702L is displayed with, but readily distinguishable from other display regions.

The operation region 710 contains a right-eye measurement display part 711R, a left-eye measurement display part 711L, and a change instruction part 712. The right-eye measurement display part 711R is a region for indicating that the right eye is currently being measured. The left-eye measurement display part 711L is a region for indicating that the left eye is currently being measured. When optometry measurements are performed automatically as in the flow of FIG. 8 under the control of the control unit 100, while the measurements are being performed for the right eye, the right-eye measurement display part 711R is displayed distinguishably from the left-eye measurement display part 711L under the control of the control unit 100. On the other hand, while the measurements are being performed for the left eye, the left-eye measurement display part 711L is displayed distinguishably from the right-eye measurement display part 711R under the control of the control unit 100. Upon detection of whether the optical system is located in front of the right eye or the left eye, the control unit 100 may determine whether the measurements are performed for the right eye or the left eye from the detection result. In this case, when the measurements are performed for the right eye, according to an instruction from the control unit 100 based on the determination result, the right-eye measurement display part 711R is displayed distinguishably from the right-eye measurement display part 711R. When the measurements are performed for the left eye, according to an instruction from the control unit 100 based on the determination result, the left-eye measurement display part 711L is displayed distinguishably from the right-eye measurement display part 711R. When optometry measurements are performed manually as in the flow of FIG. 8, while the measurements are being performed for the right eye, according to an instruction from the user, the right-eye measurement display part 711R is displayed distinguishably from the left-eye measurement display part 711L. On the other hand, while the measurements are being performed for the left eye, according to an instruction from the user, the left-eye measurement display part 711L is displayed distinguishably from the right-eye measurement display part 711R. The change instruction part 712 is an operation part for instructing a change of refractive power applied to the subject's eye E. The change instruction part 712 (the operation unit 140) is an example of "one operation unit for instructing a change of refractive power applied to the subject's eye E". Based on operation to the change instruction part 712, the control unit 100 determines whether there is an instruction to change refractive power applied to the subject's eye.

FIGS. 10 and 11 each illustrate an example of the display screen 10a, on which the right-eye measurement display part 711R is displayed distinguishably from the left-eye measurement display part 711L, in the comparison test where the measurements are performed for the right eye. When a measurement value is applied to the right eye in step S5, if the user provides an input (e.g., touch input) to the change instruction part 712 on the display screen 10a (FIG. 10), the control unit 100 controls the refractive power application unit 111b to apply the calculation value to the right eye as in the flow of FIG. 9. With this, as illustrated in FIG. 11, the right-eye calculation value display region 702R is displayed distinguishably from the right-eye subjective measurement value display region 701R on the display screen 10a.

If the user provides an input to the change instruction part 712 on the display screen 10a (FIG. 11) when a calculation value is applied to the right eye in step S5, the control unit 100 controls the refractive power application unit 111b to apply the measurement value to the right eye as in the flow of FIG. 9. With this, as illustrated in FIG. 10, the right-eye subjective measurement value display region 701R is displayed distinguishably from the right-eye calculation value display region 702R on the display screen 10a.

As described above, each time the user operates the change instruction part 712, the control unit 100 cyclically switches refractive power applied to the subject's eye to a measurement value or a calculation value. With this, the subject can easily compare the vision when the measurement value is applied with the vision when the calculation value is applied. This enables a selection of the most suitable prescription for the subject.

The ophthalmologic apparatus 1 of the embodiment includes the refractive power application unit 111b, the storage unit 120, and the control unit 100. The refractive power application unit 111b is configured to be capable of changing refractive power applied to the subject's eye E. The storage unit 120 stores at least a measurement value of eye refractive power obtained by a measurement performed for the subject's eye E in the past. In response to the input of an instruction to change refractive power applied to the subject's eye E, the control unit 100 controls the refractive power application unit 111b to selectively apply a measurement value and one or more refractive values different from the measurement value.

With this, a measurement value and one or more refractive values different from the measurement value can be selectively applied to the subject's eye by input of an instruction to change refractive power. This facilitates the comparison between the vision where a measurement value is applied and the vision where a refractive value is applied, thereby enabling a selection of the most suitable prescription for the subject.

The one or more refractive values may include a calculation value obtained based on the measurement value. With this, the measurement value and the calculation value obtained based on the measurement value can be selectively applied to the subject's eye by input of an instruction to change refractive power. This facilitates the comparison between the vision where the measurement value is applied and the vision where the calculation value is applied, thereby enabling a selection of the most suitable prescription for the subject.

The ophthalmologic apparatus 1 may include the change instruction part 712 (one operation unit) for instructing a change of refractive power applied to the subject's eye E. The control unit 100 may control the refractive power application unit 111b to sequentially apply a measurement value and one or more refractive values to the subject's eye E each time operation is performed on the change instruction part 712. With this, the measurement value and the one or more refractive values different from the measurement value can be sequentially applied to the subject's eye E each time operation is performed on the change instruction part 712. This facilitates the comparison between the vision where the measurement value is applied and the vision where the refractive value is applied, thereby enabling a selection of the most suitable prescription for the subject.

The control unit 100 may control the refractive power application unit 111b to cyclically apply a measurement value and one or more refractive values to the subject's eye E each time operation is performed on the change instruction part 712. With this, the measurement value and the one or more refractive values different from the measurement value can be cyclically applied to the subject's eye E each time operation is performed on the change instruction part 712. This facilitates the comparison between the vision where the measurement value is applied and the vision where the refractive value is applied, thereby enabling a selection of the most suitable prescription for the subject.

The ophthalmologic apparatus 1 may include the calculator 101. The calculator 101 calculates one or more calculation values based on a measurement value. This allows downsizing of the ophthalmologic apparatus that provides an easy comparison between the vision where the measurement value is applied and the vision where the calculation value is applied.

The storage unit 120 may store one or more refractive values in advance. This allows downsizing of the ophthalmologic apparatus that provides an easy comparison between the vision where the measurement value is applied and the vision where the refractive value is applied.

The measurement value may include an objective measurement value obtained by an objective measurement. This facilitates the comparison between the vision where the objective measurement value is applied and the vision where the refractive value is applied, thereby enabling a selection of the most suitable prescription for the subject.

The ophthalmologic apparatus 1 may include the objective measurement unit 112. The objective measurement unit 112 performs objective measurement for the subject's eye E. This allows downsizing of the ophthalmologic apparatus that provides an easy comparison between the vision where the objective measurement value is applied and the vision where the refractive value is applied.

The measurement value may include spherical power, degree of astigmatism, and astigmatic axis angle, and the one or more refractive values may include equivalent spherical power of the subject's eye E. This achieves the ophthalmologic apparatus that enables a comparison between the vision where the spherical power, the degree of astigmatism, and the astigmatic axis angle are applied and the vision where the equivalent spherical power of the subject's eye E is applied.

The ophthalmologic apparatus 1 may include the visual target present unit 111a. The visual target present unit 111a presents a visual target to the subject's eye E. This achieves the ophthalmologic apparatus that is capable of presenting a visual target to the subject's eye E and enables a comparison between the vision where a measurement value is applied and the vision where a refractive value is applied.

The ophthalmologic apparatus 1 includes the visual target present unit 111a, the storage unit 120, and the control unit 100. The visual target present unit 111a presents a visual target to the subject's eye E. The storage unit 120 stores at least a measurement value of eye refractive power obtained by a measurement performed for the subject's eye E in the past. According to an instruction form the operation unit 140, the control unit 100 controls the visual target present unit 111a to selectively apply a measurement value and one or more refractive values different from the measurement value to the subject's eye E. For example, the visual target present unit 111a presents a visual target by moving the focus lens 13g in the fixation target projection system 13. With this, for example, by the control of the optical system such as the focus lens 13g, a measurement value and one or more refractive values different from the measurement value can be selectively applied to the subject's eye. This facilitates the comparison between the vision where the measurement value is applied and the vision where the refractive value is applied, thereby enabling a selection of the most suitable prescription for the subject.

Modification 1 of the First Embodiment

While the first embodiment describes an example in which one or more refractive values different from a measurement value include a calculation value obtained based on the measurement value, the ophthalmologic apparatus of the embodiment is not so limited.

In this modification, the control unit 100 of the first embodiment controls the refractive power application unit 111b to selectively apply a measurement value and the naked vision or uncorrected visual acuity of the subject's eye E to the subject's eye E. That is, in the first embodiment, the one or more refractive values different from the measurement value may include the uncorrected visual acuity of the subject's eye E. The uncorrected visual acuity is an objective measurement value obtained by an objective measurement performed in the past or a subjective measurement value obtained by a subjective measurement performed for the naked eye in the past. The uncorrected visual acuity may include spherical power, degree of astigmatism, and astigmatic axis angle.

The ophthalmologic apparatus of this modification has basically the same structure as that of the first embodiment. In other words, the ophthalmologic apparatus of this modification has the same structure as illustrated in FIGS. 1 to 7. The ophthalmologic apparatus having this structure can perform tests as illustrated in FIG. 8.

As one or more refractive values different from a measurement value, the storage unit 120 stores in advance the uncorrected visual acuity of at least one of the right eye and the left eye. In the flow of FIG. 9, the uncorrected visual acuity of the subject's eye is applied in step S24 without calculation of a calculation value in step S21.

According to the modification, each time the user operates the change instruction part 712, the control unit 100 cyclically switches refractive power applied to the subject's eye E to a measurement value or the uncorrected visual acuity of the subject's eye E. With this, the subject can easily compare the vision when the measurement value is applied with the uncorrected vision. This enables a selection of the most suitable prescription for the subject.

Modification 2 of the First Embodiment

While the modification 1 of the first embodiment describes an example in which one or more refractive values different from a measurement value include the uncorrected visual acuity of the subject's eye E, the ophthalmologic apparatus of the embodiment is not so limited.

In this modification, the control unit 100 of the first embodiment controls the refractive power application unit 111b to selectively apply a measurement value and a corrected visual acuity (lens data or the like) indicating the refractive power of a refractive correction worn by the subject to the subject's eye E. That is, in the first embodiment, the one or more refractive values different from the measurement value may include a corrected visual acuity (lens data or the like) indicating the refractive power of a refractive correction worn by the subject to the subject's eye E.

The ophthalmologic apparatus of this modification has basically the same structure as that of the first embodiment. In other words, the ophthalmologic apparatus of this modification has the same structure as illustrated in FIGS. 1 to 7. The ophthalmologic apparatus having this structure can perform tests as illustrated in FIG. 8.

As one or more refractive values different from a measurement value, the storage unit 120 stores in advance the corrected visual acuity (lens data or the like) of at least one of the right eye and the left eye. In the flow of FIG. 9, the corrected visual acuity is applied in step S24 without calculation of a calculation value in step S21.

According to the modification, each time the user operates the change instruction part 712, the control unit 100 cyclically switches refractive power applied to the subject's eye to a measurement value or a corrected visual acuity. With this, the subject can easily compare the vision when the measurement value is applied with the vision corrected by the refractive power of a refractive correction worn by the subject. This enables a selection of the most suitable prescription for the subject.

Second Embodiment

In the first embodiment, the calculator 101 obtains a single calculation value from a measurement value and the control unit 100 controls the refractive power application unit 111b to alternately apply the measurement value and the calculation value to the subject's eye E. This description is by way of example and not by way of limitation. In a second embodiment, the calculator 101 obtains a plurality of calculation values from a measurement value and the control unit 100 controls the refractive power application unit 111b to cyclically apply the measurement value and the calculation values to the subject's eye E.

The ophthalmologic apparatus of the second embodiment has basically the same structure as that of the first embodiment. In other words, the ophthalmologic apparatus of the second embodiment has the same structure as illustrated in FIGS. 1 to 7. The ophthalmologic apparatus having this structure can perform tests as illustrated in FIG. 8. In the following description of the ophthalmologic apparatus of the second embodiment, the difference from the first embodiment is mainly described using the same reference numerals as in the first embodiment.

Figure 12:
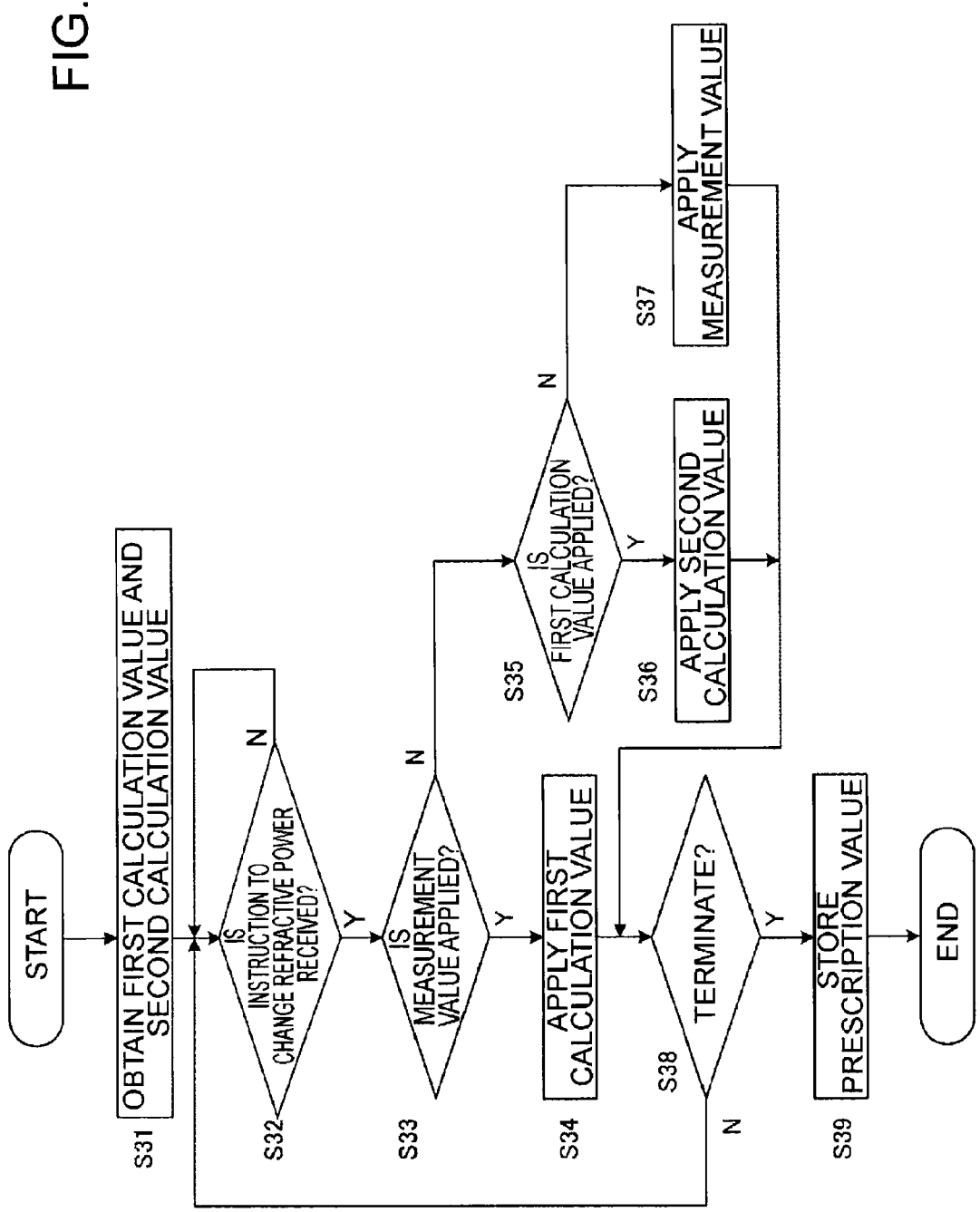
FIG. 12 is a flowchart of an example of the operation of an ophthalmologic apparatus according to an embodiment.

FIG. 12 is a flowchart of a comparison test performed in step S5 of the second embodiment. The comparison test in step S11 of FIG. 8 is performed in the same flow as illustrated in FIG. 12. FIG. 12 illustrates an example in which the control unit 100 controls the refractive power application unit 111b to cyclically apply a measurement value and a plurality of calculation values obtained based on the measurement value to the right eye.

(S31)

In step S5 in FIG. 8, the calculator 101 obtains a plurality of calculation values based on the measurement value obtained by the objective measurement in step S2 or the subjective measurement in step S4. The calculator 101 obtains the calculation values from the measurement value obtained in step S2 or S4 using a predetermined formula. For example, the calculator 101 may find equivalent spherical power from spherical power and degree of astigmatism obtained in step S2 or S4 using formula (1), and add a plurality of correction values to the equivalent spherical power to obtain the calculation values. The control unit 100 stores each of the calculation values obtained by the calculator 101 in the storage unit 120 together with type information thereof. It is assumed herein that the calculator 101 obtains a first calculation value and a second calculation value based on the measurement value obtained by the objective measurement in step S2 or the subjective measurement in step S4 using a predetermined formula. For example, the first calculation value may be equivalent spherical power obtained by formula (1), while the second calculation value may be a value obtained by adding a predetermined correction value to the first calculation value. Note that the timing of this calculation is not necessarily in immediately before step S32. The calculation may be performed in arbitrary timing before step S34 or S36 described below.

(S32)

The control unit 100 waits for an instruction from the user to change refractive power through the operation unit 140 (N in S32). Upon receipt of an instruction from the user to change refractive power through the operation unit 140 (Y in S32), the process control of the control unit 100 moves to step S33.

(S33)

Upon receipt of an instruction from the user to change refractive power through the operation unit 140 (Y in S32), the control unit 100 determines whether the measurement value obtained by the objective measurement in step S2 or the subjective measurement in step S4 is applied to the right eye. If it has been determined that the measurement value is applied to the right eye (Y in S33), the process control of the control unit 100 moves to step S34. If not (N in S33), the process control moves to step S35.

(S34)

Having determined that the measurement value is applied to the right eye (Y in S33), the control unit 100 controls the refractive power application unit 111b to apply the first calculation value obtained in step S31 to the right eye. Then, the process control of the control unit 100 moves to step S38.

(S35)

Having determined that the measurement value is not applied to the right eye (N in S33), the control unit 100 determines whether the first calculation value obtained in step S31 is applied to the right eye. If it has been determined that the first calculation value is applied to the right eye (Y in S35), the process control of the control unit 100 moves to step S36. If not (N in S35), the process control moves to step S37.

(S36)

Having determined that the first calculation value is applied to the right eye (Y in S35), the control unit 100 controls the refractive power application unit 111b to apply the second calculation value obtained in step S31 to the right eye. Then, the process control of the control unit 100 moves to step S38.

(S37)

Having determined that the first calculation value is not applied to the right eye (N in S35), the control unit 100 determines that the second calculation value obtained in step S31 is applied to the right eye. The control unit 100 controls the refractive power application unit 111b to apply the measurement value obtained in step S2 or S4 to the right eye. The process control of the control unit 100 moves to step S38.

(S38)

For example, based on an instruction from the user received through the operation unit 140, the control unit 100 determines whether to terminate the comparison test. If the control unit 100 determines to terminate the comparison test (Y in S38), the process control of the control unit 100 moves to step S39. If not (N in S38), the process control loops back to step S32.

(S39)

Having determined to terminate the comparison test (Y in S38), the control unit 100 determines the measurement value or the calculation value selected by the subject as a prescription value for the right eye. The control unit 100 stores the prescription value for the right eye in the storage unit 120. With this, the process control for the comparison test ends (End).

The ophthalmologic apparatus 1 of the embodiment includes the refractive power application unit 111b, the storage unit 120, and the control unit 100. The refractive power application unit 111b is configured to be capable of changing refractive power applied to the subject's eye E. The storage unit 120 stores at least a measurement value of eye refractive power obtained by a measurement performed for the subject's eye E in the past. In response to the input of an instruction to change refractive power applied to the subject's eye E, the control unit 100 controls the refractive power application unit 111*b* to selectively apply a measurement value and a plurality of calculation values obtained based on the measurement value.

With this, a measurement value and a plurality of calculation values obtained based on the measurement value can be selectively applied to the subject's eye by input of an instruction to change refractive power. This facilitates the comparison between the vision where a measurement value is applied and the vision where a calculation value obtained based on the measurement value is applied, thereby enabling a selection of the most suitable prescription for the subject.

Third Embodiment

In the first and the second embodiments, a measurement value obtained by an objective measurement or a subjective measurement and one or more calculation values obtained from the measurement value are cyclically applied to the subject's eye in response to an instruction from the user to change refractive power. This description is by way of example and not by way of limitation. In a third embodiment, far sight power (far visual acuity) obtained by a far vision test and near sight power (near visual acuity) obtained by a near vision test are alternately applied to the subject's eye in response to an instruction from the user.

The ophthalmologic apparatus of the third embodiment has basically the same structure as that of the first embodiment. In other words, the ophthalmologic apparatus of the third embodiment has the same structure as illustrated in FIGS. 1 to 7. The ophthalmologic apparatus having this structure can perform tests as illustrated in a flowchart described below. In the following description of the ophthalmologic apparatus of the third embodiment, the difference from the first embodiment is mainly described using the same reference numerals as in the first embodiment.

Figure 13:
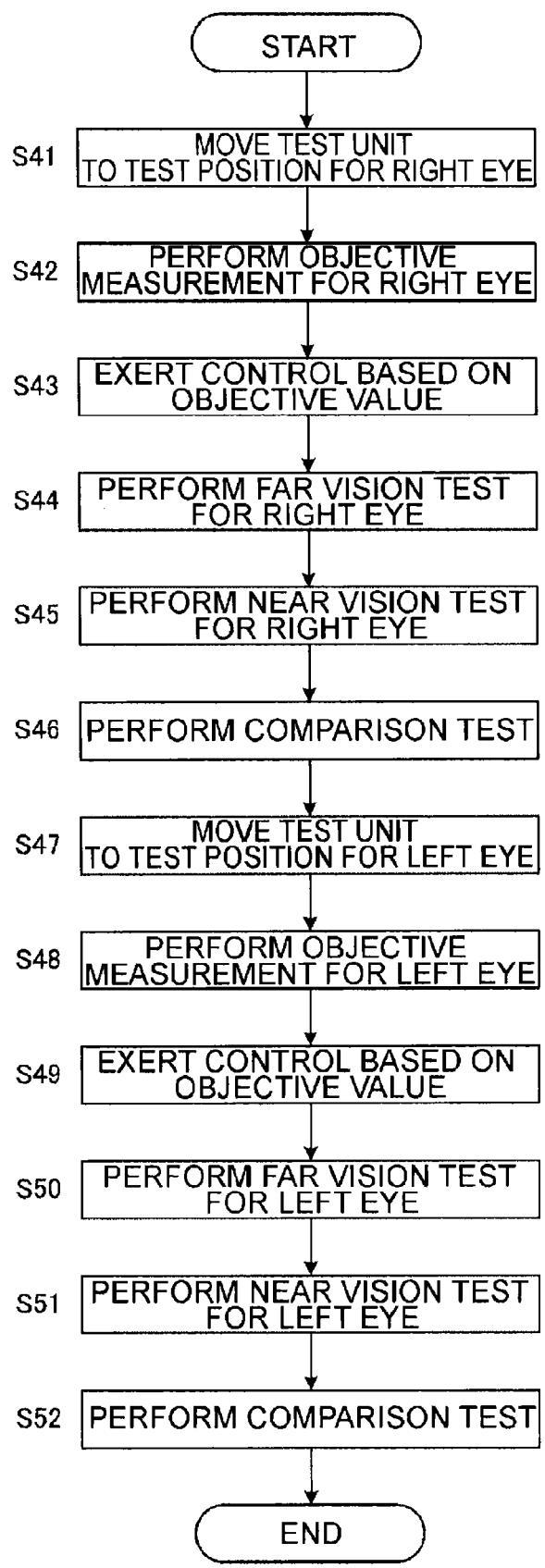
FIG. 13 is a flowchart of an example of the operation of an ophthalmologic apparatus according to an embodiment.

FIG. 13 is a flowchart of a test performed by the ophthalmologic apparatus of the third embodiment. In this example, objective measurement (objective refractivity measurement) and subjective measurement (subjective refractivity measurement) are performed in this order for the right eye, and then objective measurement and subjective measurement are performed in this order for the left eye. In the subjective measurement, a far vision test and a near vision test are conducted in this order.

(S41)

After the face of the subject is fixed by the face support 5, the test unit 110 (the head 4) is moved to a test position for the right eye. The test unit 110 is moved by the control unit 100 according to operation or instruction from a user, or instruction by the control unit 100. That is, the test unit 110 is moved to the test position for the right eye and a preparation is made for objective refractivity measurement.

(S42)

After the test unit 110 is situated in the test position for the right eye, objective measurement is performed for the right eye. An objective value (measurement value) obtained by the objective measurement for the right eye is stored in the storage unit 120 by the control unit 100.

(S43)

The control unit 100 exerts control based on the objective value for the right eye obtained in step S42. The control includes, for example, the process of selecting a visual target to be presented first in subjective refractivity measurement (far vision test, near vision test) sequentially performed thereafter.

(S44)

According to an instruction from the user or the control unit 100, the test unit 110 selectively presents various visual targets to the right eye. The user or the ophthalmologic apparatus 1 obtains a far sight power (far visual acuity) of the right eye based on a response to the visual targets from the subject. The control unit 100 stores the far sight power in the storage unit 120.

(S45)

After the completion of the far vision test for the right eye, a near vision test is performed for the right eye. The control unit 100 controls the test unit 110 to prepare for the near vision test. According to an instruction from the user or the control unit 100, the test unit 110 selectively presents various visual targets to the right eye. The user or the ophthalmologic apparatus 1 obtains a near sight power (near visual acuity) of the right eye based on a response to the visual targets from the subject. The control unit 100 stores the near sight power in the storage unit 120.

(S46)

Subsequently, the control unit 100 controls the refractive power application unit 111*b* to alternately apply the measurement value (far sight power) obtained by the far vision test in step S44 and the measurement value (near sight power) obtained by the near vision test in step S45 to the right eye. This allows the subject to check differences in visions with respect to the far sight power and the near sight power. The subject selects desired one of the far sight power and the near sight power applied to the right eye in step S46, and the control unit 100 stores the desired value in the storage unit 120 as a prescription value of the right eye. An example of the control of the control unit 100 in step S46 is described later (see FIG. 14).

(S47)

After completion of the near vision test for the right eye, the test unit 110 is moved to a test position for the left eye.

(S48)

After the test unit 110 is situated in the test position for the left eye, objective refractivity measurement is performed for the left eye. An objective value (measurement value) obtained by the objective measurement for the left eye is stored in the storage unit 120.

(S49)

As in step S43, the control unit 100 exerts control based on the objective value for the left eye obtained in step S48. The control includes, for example, the process of selecting a visual target to be presented first in subjective refractivity measurement (far vision test, near vision test) sequentially performed thereafter.

(S50)

A far vision test is performed for the left eye in the same manner as that for the right eye. A far sight power obtained by the test is stored in the storage unit 120.

(S51)

After the completion of the far vision test for the left eye, a near vision test is performed for the left eye in the same manner as that for the right eye. A near sight power obtained by the test is stored in the storage unit 120.

(S52)

Subsequently, the control unit 100 controls the refractive power application unit 111*b* to alternately apply the far sight power obtained by the far vision test in step S50 and the near sight power obtained by the near vision test in step S51 to the left eye. This allows the subject to check differences in visions with respect to the far sight power and the near sight power. The subject selects desired one of the far sight power and the near sight power applied to the left eye in step S52, and the control unit 100 stores the desired value in the storage unit 120 as a prescription value of the left eye. An example of the control of the control unit 100 in step S52 is the same as in step S46. Thus, this process ends.

In the flow of FIG. 13, a comparison test based on the far visual acuity may be performed as in the flow of FIG. 8. Besides, a comparison test may be performed based on the near visual acuity obtained by the near vision test in step S46 or S51.

Further, a contrast test and/or a glare test may be performed in arbitrary timing in the flowchart of FIG. 13 as in FIG. 8.

Figure 14:
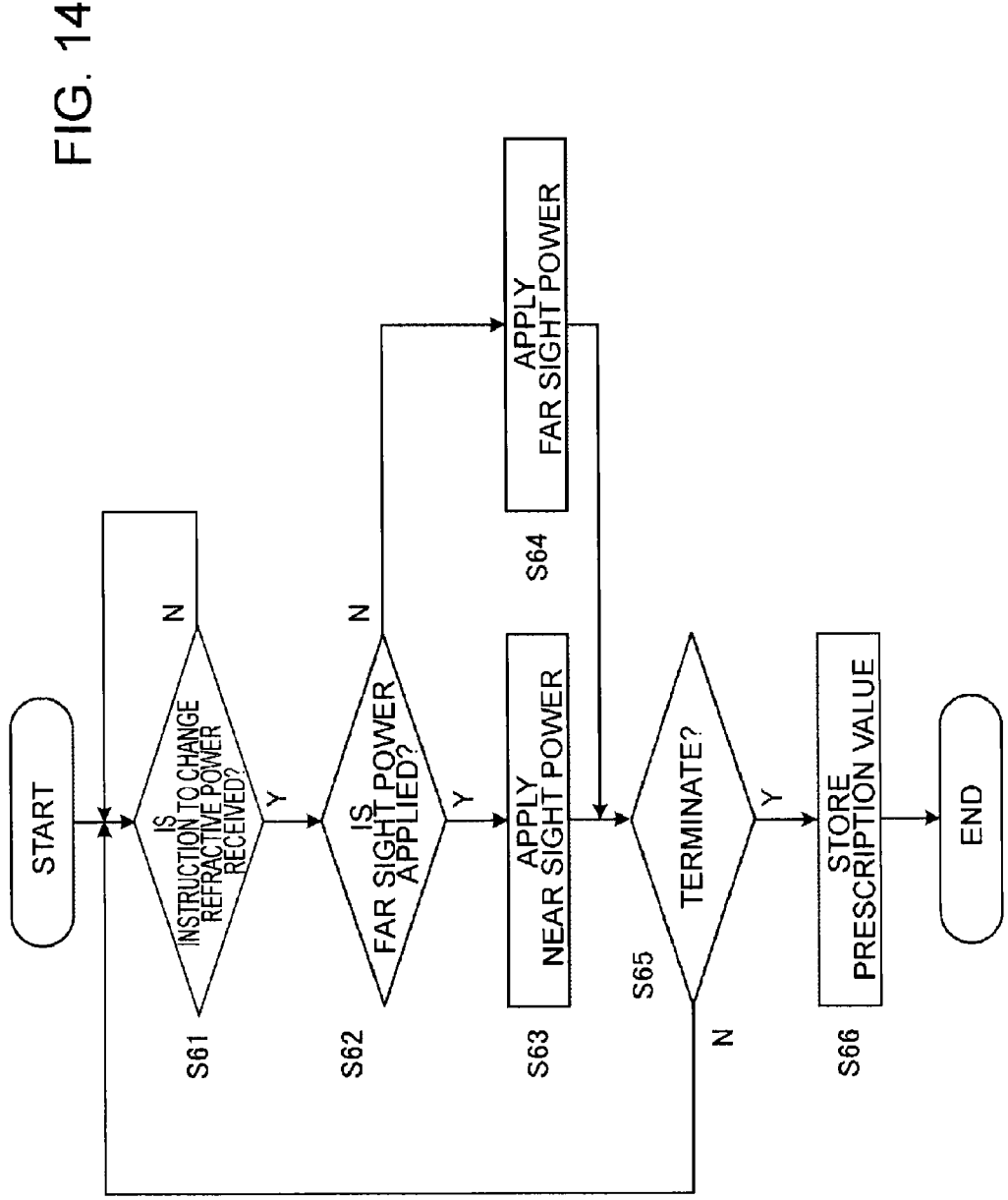
FIG. 14 is a flowchart of an example of the operation of an ophthalmologic apparatus according to an embodiment.

FIG. 14 is a detailed flowchart of the comparison test performed in step S46 in FIG. 13. The comparison test in step S52 of FIG. 13 is performed in a similar manner.

(S61)

Before step S46 of FIG. 13, the control unit 100 stores the far sight power and the near sight power of the right eye in the storage unit 120. The control unit 100 waits for an instruction from the user to change refractive power through the operation unit 140 (N in S61). Upon receipt of an instruction from the user to change refractive power through the operation unit 140 (Y in S61), the process control of the control unit 100 moves to step S62.

(S62)

Upon receipt of an instruction from the user to change refractive power through the operation unit 140 (Y in S61), the control unit 100 determines whether the far sight power obtained by the far vision test in step S44 is applied to the right eye. If it is determined that the far sight power is applied to the right eye (Y in S62), the process control of the control unit 100 moves to step S63. If not (N in S62), the process control moves to step S64.

(S63)

Having determined that the far sight power is applied to the right eye (Y in S62), the control unit 100 controls the refractive power application unit 111b to apply the near sight power obtained by the near vision test in step S45 to the right eye. Then, the process control of the control unit 100 moves to step S65.

(S64)

Having determined that the far sight power is not applied to the right eye (N in S62), the control unit 100 determines that the near sight power obtained in step S45 is applied to the right eye. The control unit 100 controls the refractive power application unit 111b to apply the far sight power obtained in step S44 to the right eye. The process control of the control unit 100 moves to step S65.

(S65)

For example, based on an instruction from the user received through the operation unit 140, the control unit 100 determines whether to terminate the comparison test. If the control unit 100 determines to terminate the comparison test (Y in S65), the process control of the control unit 100 moves to step S66. If not (N in S65), the process control loops back to step S61.

(S66)

Having determined to terminate the comparison test (Y in S65), the control unit 100 determines the far sight power or the near sight power selected by the subject as a prescription value for the right eye. The control unit 100 stores the prescription value for the right eye in the storage unit 120. With this, the process control for the comparison test ends (End).

As described above, each time the user operates the change instruction part 712, the control unit 100 alternately switches refractive power applied to the subject's eye between far sight power and near sight power. With this, the subject can easily compare the vision when the far sight power obtained by a far vision test is applied with the vision when the near sight power obtained by a near vision test is applied. This enables a selection of the most suitable prescription for the subject.

The ophthalmologic apparatus 1 of the embodiment includes the visual target present unit 111a, the refractive power application unit 111b, the storage unit 120, and the control unit 100. The visual target present unit 111a presents a visual target to the subject's eye E. The refractive power application unit 111b is configured to be capable of changing refractive power applied to the subject's eye E. The storage unit 120 stores a far sight power and a near sight power obtained by a measurement performed for the subject's eye E in the past. In response to the input of an instruction to change refractive power applied to the subject's eye E, the control unit 100 controls the refractive power application unit 111b to alternately apply the far sight power and the near sight power to the subject's eye E.

With this, a far sight power and a near sight power can be alternately applied to the subject's eye by input of an instruction to change refractive power. This facilitates the comparison between the vision where a far sight power is applied and the vision where a near sight power is applied, thereby enabling a selection of the most suitable prescription for the subject.

Fourth Embodiment

In the first to third embodiments, a description is given of a case where a far vision test using a visual target spatially or optically arranged at a first distance (e.g., 5 meters, etc.) and a near vision test using a visual target spatially or optically arranged at a second distance (e.g., 30 centimeters, etc.) are conducted. However, this is by way of example and not by way of limitation. In a fourth embodiment, the ophthalmologic apparatus is capable of performing intermediate vision tests for obtaining the visual acuity of the subject's eye and the power of a prescribed lens using a visual target spatially or optically arranged at a third distance (shorter than the first distance and longer than the second distance, e.g., 1 meter, 2 meters, 3 meters, etc.).

The ophthalmologic apparatus of the fourth embodiment is capable of performing intermediate vision tests for obtaining the visual acuity of the subject's eye and the power of a prescribed lens using a visual target spatially or optically arranged at the third distance by moving the focus lens 13g illustrated in FIGS. 2 to 5.

For example, an intermediate test mode instruction part may be provided in the operation region 710 on the display screen 10a illustrated in FIG. 10 or 11. When the user operates the intermediate test mode instruction part, the control unit 100 moves the focus lens 13g to a position where a visual target is optically arranged at the third distance. During the intermediate test mode in which a visual target is optically arranged at the third distance, the control unit 100 controls the refractive power application unit 111b to selectively apply a measurement value and one or more refractive values different from the measurement value in response to the input of an instruction to change refractive power applied to the subject's eye E.

For another example, a test mode switch instruction part may be provided in the operation region 710 on the display screen 10a illustrated in FIG. 10 or 11. Each time the user operates the test mode switch instruction part, the control unit 100 cyclically moves the focus lens 13g to a first position where a visual target is optically arranged at the first distance, a second position where a visual target is optically arranged at the second distance, a third position where a visual target is optically arranged at the third distance. In each of the far vision test where the focus lens 13g is arranged at the first position, the near vision test where the focus lens 13g is arranged at the second position, and the intermediate vision test where a visual target is optically arranged at the third distance, the control unit 100 controls the refractive power application unit 111b to selectively apply a measurement value and one or more refractive values different from the measurement value to the subject's eye in response to the input of an instruction to change refractive power applied to the subject's eye E. The control unit 100 may control the refractive power application unit 111b to change the additional power applied to the subject's eye depending on the test mode.

Further, for example, the focus lens 13g may be moved to an arbitrary position by user operation on the operation unit 140. As the focus lens 13g has been moved to an arbitrary position by user operation, the control unit 100 controls the refractive power application unit 111b to selectively apply a measurement value and one or more refractive values different from the measurement value to the subject's eye in response to the input of an instruction to change refractive power applied to the subject's eye E. The control unit 100 may control the refractive power application unit 111b to change the additional power applied to the subject's eye depending on the position of the focus lens 13g.

In this embodiment also, the one or more refractive values different from the measurement value may include one or more of the uncorrected visual acuity of the subject's eye E, a corrected visual acuity indicating the refractive power of a refractive correction worn by the subject, and a calculation value based on the measurement value.

In general, with a progressive lens that covers a range of vision from far to near, the eyesight is narrower in the near vision. If the purposes of the subject to wear a refractive correction are narrowed down, it is possible to create a suitable refractive correction capable of providing wide eyesight as progressive lenses for near/near vision. For example, if a range of vision from far to near is desired, a bifocal lens for far/near vision is created. If a refractive correction is used only at home, a progressive power lens for middle/near vision is created. If a refractive correction is not used for detailed work, a progressive lens for near/near vision is created. According to the embodiment, upon creating a refractive correction such as glasses, tests can be conducted for a distance depending on the intended use.

Fifth Embodiment

In the first to fourth embodiments, a description is given of the ophthalmologic apparatus having the structure as illustrated in FIGS. 1 to 7 and capable of subjective measurements and objective measurements. However, the ophthalmologic apparatus of the embodiments is not so limited. The ophthalmologic apparatus of the fifth embodiment is capable of only subjective measurements.

Figure 15:
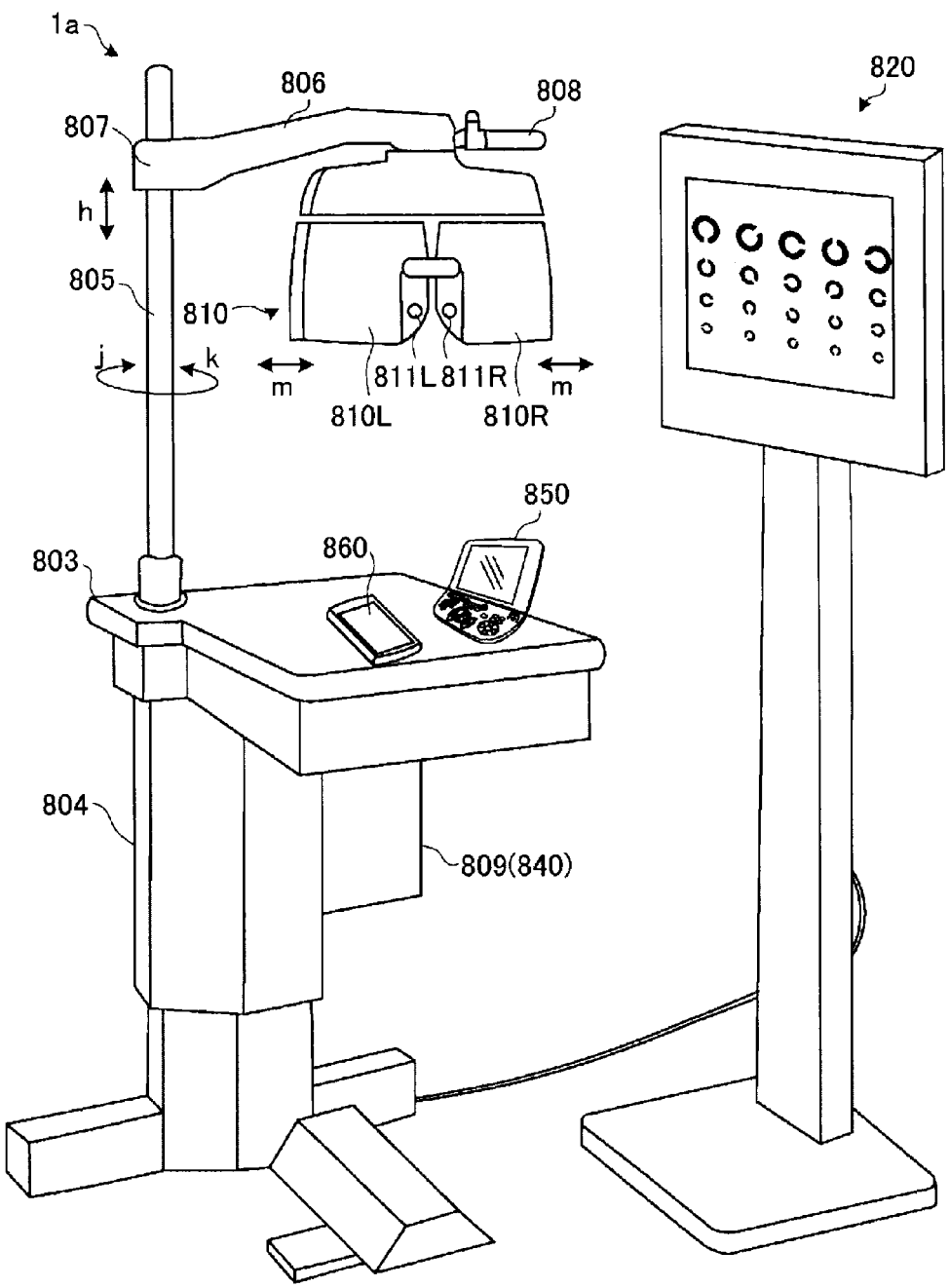
FIG. 15 is a schematic view of an example of an ophthalmologic apparatus according to an embodiment.

FIG. 15 is a schematic external view of the ophthalmologic apparatus of the fifth embodiment. Although FIG. 15 illustrates a tablet terminal and a controller as the operation unit to operate the ophthalmologic apparatus, either one of them is sufficient as the operation unit of the ophthalmologic apparatus of the fifth embodiment. FIG. 16 is a functional block diagram of an example of a control system in the ophthalmologic apparatus illustrated in FIG. 15. Like reference numerals refer to like parts in FIGS. 15 and 16, and the same description may not be repeated.

An ophthalmologic apparatus 1a is used to test the visual acuity, visual performance, and the like by presenting a visual target to the subject's eye through an optical element. The ophthalmologic apparatus 1a includes a measurement head 810 (refractor, phoropter), a visual target present device 820, a main controller 840, a controller 850, and a tablet terminal 860. The ophthalmologic apparatus 1a need not necessarily include all the measurement head 810, the visual target present device 820, the main controller 840, the controller 850, and the tablet terminal 860.

The measurement head 810, the visual target present device 820, the main controller 840, and the controller 850 are electrically connected via a cable including a power wire and a communication wire. The power wire is used to provide each unit with power from the main controller 840. The communication wire is used for communications between the main controller 840 and each unit. The tablet terminal 860 is configured to be capable of communicating with the main controller 840 via a wireless communication link. The main controller 840 is configured to be capable of establishing a wireless communication link with at least one tablet terminal (860).

In the example of FIG. 15, the ophthalmologic apparatus 1a includes an optometry table 803. The optometry table 803 is used to support the measurement head 810, place the controller 850, and the like. The optometry table 803 is provided as being supported by a support 804 on the floor. In the example of FIG. 15, the controller 850 and the tablet terminal 860 are placed on the optometry table 803.

For example, a support column 805 is provided on the optometry table 803. An end of the support column 805 is inserted in a hollow support portion 807 provided in one end of a horizontal arm 806. The support column 805 supports the horizontal arm 806 such that the horizontal arm 806 is movable in the vertical direction (arrow direction h) and rotatable about an axis (rotatable in arrow directions j and k). The measurement head 810 is held at the other end of the horizontal arm 806. An operation arm 808 sticks out from the other end. The operation arm 808 is operated by the operator to rotate the horizontal arm 806 and the measurement head 810 about the axis of the support column 805. The horizontal arm 806 may have a mechanism to rotate the measurement head 810 about a horizontal axis. A storage 809 is provided to a side surface of the support 804 to install the main controller 840. Note that the structure of the optometry table 803 is not limited to the illustration of FIG. 15.

In this embodiment, the tablet terminal 860 and the controller 850 are the operation unit for controlling the ophthalmologic apparatus 1a. The measurement head 810 selectively applies a plurality of optical elements to the subject's eye according to operator's operation on the tablet terminal 860 or the controller 850. The visual target present device 820, for example, selectively presents a plurality of visual targets to the subject's eye according to operator's operation on the tablet terminal 860 or the controller 850. The main controller 840 controls at least one of the measurement head 810 and the visual target present device 820 in response to operator's operation on the tablet terminal 860 or the controller 850.

The main controller 840 is capable of controlling the measurement head 810 or the visual target present device 820 without priority control for operations received substantially at the same time on the tablet terminal 860 and the controller 850 within a predetermined period of time. The main controller 840 may perform priority control based on a priority order determined in advance for operations received substantially at the same time on the tablet terminal 860 and the controller 850 within a predetermined period of time. In this case, the main controller 840 controls the measurement head 810 or the visual target present device 820 according to operation having a higher priority based on the priority order determined in advance.

(Measurement Head)

The measurement head 810 is capable of selectively arranging a plurality of optical elements for the subject's eye. The measurement head 810 includes a left-eye optometry unit 810L and a right-eye optometry unit 810R. Each of the left-eye optometry unit 810L and the right-eye optometry unit 810R is provided with a plurality of built-in optical elements selectively applied to the subject's eye. The left-eye optometry unit 810L applies selected one or more of the optical elements to the left eye of the subject (left subject's eye). The right-eye optometry unit 810R applies selected one or more of the optical elements to the right eye of the subject (right subject's eye). The left-eye optometry unit 810L and the right-eye optometry unit 810R have optometry windows 811L and 811R, respectively. In response to operation on the tablet terminal 860 and the controller 850, the optical elements are selectively arranged at the optometry windows 811L and 811R. The left subject's eye views a visual target presented by the visual target present device 820 through the optometry window 811L. The right subject's eye views a visual target presented by the visual target present device 820 through the optometry window 811R.

The left-eye optometry unit 810L and the right-eye optometry unit 810R are configured to operate individually. Each of the optometry units has a plurality of optical elements and a drive mechanism.

The optical elements of the optometry units are a group of various types of lenses for testing the visual performance of the subject's eye. The optical elements include, for example, at least one of a spherical lens, a cylindrical lens, a progressive lens, and a prism lens. The optical elements are classified according to the types of optometry parameters.

The optometry parameters indicate test conditions for testing the visual performance of the subject's eye. For example, the types of the optometry parameters include at least one of spherical power, degree of astigmatism, astigmatic axis angle, additional power, pupillary distance, prism power, and prism direction. As an exemplified classification of the optometry parameters, a group related to spherical power includes a plurality of spherical lenses having different spherical powers. A group related to the degree of astigmatism includes a plurality of cylindrical lenses having different degrees of astigmatism. The group related to the degree of astigmatism may be further classified according to astigmatic axis angle. A group related to additional power includes a plurality of progressive lenses having different additional powers. A group related to prism power includes a plurality of prism lenses having different prism powers. The group related to prism power may be further classified according to prism direction. The pupillary distance is a test condition set in conformity to the pupillary distance of the subject's eyes. The pupillary distance is set by the slide movement of either or both the left-eye optometry unit 810L and the right-eye optometry unit 810R in the horizontal direction (arrow direction m in FIG. 15).

The drive mechanism of each optometry unit is configured to be capable of arranging each of the optical elements at the optometry window as well as retracting it therefrom. The drive mechanism includes, for example, a plurality of turret boards having a disk shape. In the drive mechanism, the turret boards are configured to be rotatable about the center of the circle in the circumferential directions. The turret boards have a plurality of holes near the periphery. An optical element fits in each of the holes. The drive mechanism arranges each of the optical elements at the optometry window and retracts it therefrom by rotating the turret boards.

The measurement head 810 is capable of switching the optical elements from one to another to apply at least one of spherical power, degree of astigmatism, astigmatic axis angle, additional power, pupillary distance, prism power, and prism direction to the subject's eye under the control of the main controller 840. As described above, the measurement head 810 is configured to be capable of changing refractive power applied to the subject's eye. The measurement head 810 is an example of "refractive power application unit" in this embodiment.

(Visual Target Present Device)

The visual target present device 820 is placed in a position in front of and at a predetermined distance from the measurement head 810. The visual target present device 820 displays one or more switchable visual targets to present the visual targets to the subject's eye. The visual target present device 820 is capable of displaying such visual targets as vision test visual targets, red-green test visual targets, astigmatism test visual targets, and the like in response to a control signal from the main controller 840. According to a control signal from the main controller 840, the visual target present device 820 may display visual targets in a predetermined order, or display a visual target specified by the control signal. As described above, the visual target present device 820 presents a plurality of visual targets including near vision visual targets to the subject's eye. The visual target present device 820 is an example of "visual target present unit" in this embodiment.

(Main Controller)

The main controller 840 controls each unit of the ophthalmologic apparatus 1a. The main controller 840 receives from the controller 850 operation information corresponding to operation performed on the controller 850, and controls each unit of the ophthalmologic apparatus 1a. Specifically, the main controller 840 establishes a wired communication link with the controller 850 via a cable. While being communicably connected to the controller 850, the main controller 840 receives, from the controller 850, operation information corresponding to operation performed on the controller 850. The main controller 840 controls either or both the measurement head 810 and the visual target present device 820 based on the operation information.

In addition, the main controller 840 receives from the tablet terminal 860 operation information corresponding to operation performed on the tablet terminal 860, and controls each unit of the ophthalmologic apparatus 1a. Specifically, the main controller 840 establishes a wireless communication link with the tablet terminal 860. While being communicably connected to the tablet terminal 860, the main controller 840 receives, from the tablet terminal 860, operation information corresponding to operation performed on the tablet terminal 860. The main controller 840 controls either or both the measurement head 810 and the visual target present device 820 based on the operation information.

The main controller 840 controls the visual target present device 820 to present visual targets to the subject's eye according to control information indicating predetermined visual targets and the order in which the visual targets are presented. The main controller 840 may control the visual target present device 820 to present a visual target to the subject's eye specified by operation performed on the tablet terminal 860 or the controller 850.

The main controller 840 includes a computer having a central processing unit (CPU) and a memory. The memory stores a computer program (ophthalmologic apparatus control program) in advance. The CPU loads the control program into the memory and executes it, thereby controlling the measurement head 810 and the visual target present device 820. The memory stores a measurement value of eye refractive power obtained by a measurement performed for the subject's eye in the past. The main controller 840 may control the measurement head 810 and the visual target present device 820 by dedicated hardware.

(Controller)

The controller 850 includes an operation unit and a display unit. The operation unit includes a plurality of switches and a single dial, and receives operations such as press of the switches and rotation of the dial. The switches include a switch for switching test parameters, a switch for changing the switching direction of the test parameters, a switch for changing the eye to be tested, a switch for moving a switching object, and a switch for changing test type. The switching direction includes a positive direction for changing the test parameters in a predetermined direction and a negative direction for changing the test parameters in a direction opposite to the positive direction. According to the amount of the rotation of the dial, optometry parameters and the types of the optometry parameters are changed. Upon receipt of such operator's operation as above on the operation unit, the controller 850 feeds the main controller 840 with operation information corresponding to the operation. Having received the operation information from the controller 850, the main controller 840 controls the measurement head 810 and the visual target present device 820.

The display unit displays values of optometry parameters, which are parameters of optical characteristics of optical elements set at the optometry windows of the measurement head 810, as optical characteristics data for each type of the optometry parameters. The display unit also displays visual targets presented by the visual target present device 820 or a visual target chart. The display unit may display values of switchable optometry parameters, types of optometry parameters, visual targets, and visual target charts. The display unit displays various types of information under the control of the main controller 840.

(Tablet Terminal)

The tablet terminal 860 includes a display panel having a touch panel function. As well as functioning as a display unit that displays operation screen, the display panel functions as an operation unit that receives gesture operation (touch operation) by the operator. Although the touch operation is described as being performed by touching the operation surface, it may include operation performed near but not touching the operation surface. The operation screen displayed on the display panel as the display unit realizes the functions of at least part of the switches provided to the operation unit of the controller 850.

As the operation unit, the display panel has an operation surface (detection surface) capable of detecting the touch of operator's finger or a stylus. The gesture operation includes such operations on the operation surface as, for example, pinch in, pinch out, flick, tap, drag, and swipe. Pinch in is a gesture made by the operator with two fingers pinched together on the operation surface. Pinch out is a gesture made by the operator with two fingers spread apart on the operation surface. Flick is a gesture made by the operator flicking his/her finger quickly across the operation surface. Tap is a gesture made by the operator tapping his/her finger on the operation surface. Drag is a gesture made by the operator dragging his/her finger from a touch point to another on the operation surface. Swipe is a gesture made by the operator swiping his/her finger across the operation surface. For example, the operation unit of the tablet terminal detects a touch through touch sensing technology such as capacitive, resistive, surface acoustic wave, and the like.

Upon receipt of such operator's gesture operation on the display panel as above, the tablet terminal 860 sends operation information (control signal) corresponding to the operation to the main controller 840 via the communication link previously established.

The tablet terminal 860 is a controller for the ophthalmologic apparatus having CPU and a memory. The memory stores a computer program (ophthalmologic apparatus control program) in advance. The CPU loads the computer program into the memory and executes it, thereby issuing a control signal for instructing a switch of the measurement head 810 and the visual target present device 820. The tablet terminal 860 may issue a control signal for instructing a switch of the measurement head 810 and the visual target present device 820 by dedicated hardware.

The controller 850 or the tablet terminal 860 is an example of "change instruction part (operation unit)" for inputting an instruction to change to change refractive power in the above embodiments.

In the structure illustrated in FIGS. 15 and 16, the main controller 840 has the functions of the storage unit 120 and the control unit 100 of the first or second embodiment. Specifically, the main controller 840 includes the storage unit that stores a measurement value of eye refractive power obtained by a measurement performed for the subject's eye in the past, and the control unit that controls the refractive power application unit to cyclically apply a measurement value and a refractive value different from the measurement value to the subject's eye.

In the structure illustrated in FIGS. 15 and 16, the main controller 840 may have the functions of the storage unit 120 and the control unit 100 of the third embodiment. More specifically, the main controller 840 may include the storage unit that stores far sight power and near sight power obtained by measurements performed for the subject's eye in the past, and the control unit that controls the refractive power application unit to alternately apply the far sight power and the near sight power to the subject's eye in response to the input of an instruction to change refractive power applied to the subject's eye.

As described above, each time the user operates the change instruction part with respect to the measurement head 810, the main controller 840 may control the refractive power application unit to cyclically apply a measurement value obtained by a subjective measurement and one or more calculation values obtained based on the measurement value to the subject's eye. This facilitates the comparison between the vision where a measurement value is applied and the vision where a calculation value is applied, thereby enabling a selection of the most suitable prescription for the subject.

Alternatively, each time the user operates the change instruction part with respect to the measurement head 810, the main controller 840 may control the refractive power application unit to alternately apply far sight power and near sight power to the subject's eye. With this, the subject can easily compare the vision when the far sight power obtained by a far vision test is applied with the vision when the near sight power obtained by a near vision test is applied. This enables a selection of the most suitable prescription for the subject.

The ophthalmologic apparatus of this embodiment achieves the same effect as that of the first embodiment and the modifications thereof, the second embodiment, and the third embodiment.

(Other Modifications)

The embodiments described above are by way of example only, and are susceptible to various modifications and alternative forms. This disclosure is intended to cover all modifications, equivalents and alternatives falling within the scope of the present invention as defined by the appended claims.

In the above embodiments, while spherical power, degree of astigmatism, and equivalent spherical power are exemplified as calculation values obtained based on measurement values, the calculation values are not so limited.

In the above embodiments and modifications thereof, an example is described in which a measurement value and one or more refractive values different from the measurement value are selectively applied to the subject's eye in response to the input of an instruction from the user (operator) to change refractive power. However, this is not intended to impose any limitations on the embodiments. For example, a measurement value and one or more refractive values different from the measurement value may be selectively applied to the subject's eye in response to the input of an instruction from the subject. Further, the control unit 100 may selectively apply a measurement value and one or more refractive values different from the measurement value to the subject's eye in predetermined timing or arbitrary timing, for example.

In the above embodiments and modifications thereof, an example of the ophthalmologic apparatus is described that is capable of at least subjective refractivity measurement, and further capable of objective refractivity measurement (and corneal shape measurement). However, the ophthalmologic apparatus to which the present invention is applicable is not so limited. The present invention is applicable to any apparatus having a function usable in the ophthalmology field, such as, for example, intraocular pressure measurement function, fundus photographing function, anterior eye photographing function, OCT function, ultrasonography function, and the like. Incidentally, the intraocular pressure measurement function is realized by a tonometer and the like. The fundus photographing function is realized by a fundus camera, a scanning laser ophthalmoscope (SLO), and the like. The anterior eye photographing function is realized by a slit lamp microscope and the like. The OCT function is realized by OCT and the like. The ultrasonography function is realized by an ultrasonic diagnosis apparatus and the like. The present invention is also applicable to any apparatus (multifunction products) having two or more of the functions as described above.

The various features of the first to fifth embodiments and the modifications of the first embodiment may be variously combined with some features included and others excluded to suit a variety of different applications. For example, in a system to which two or more of the first to fifth embodiments and the modifications thereof are applicable, desired ones of the two or more embodiments can be alternatively applied by switching the operation mode.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmologic apparatus comprising:
a refractive power application unit configured to be capable of changing refractive power applied to a subject's eye;
a storage unit configured to store at least spherical power, degree of astigmatism, and astigmatic axis angle as a measurement value of eye refractive power obtained by a measurement performed for the subject's eye in a past;
a calculator configured to obtain one or more refractive values including equivalent spherical power based on the measurement value; and
a control unit configured to control the refractive power application unit to selectively apply the measurement value and the one or more refractive values different from the measurement value to the subject's eye to which a same visual target is being presented in response to input of an instruction to change refractive power applied to the subject's eye.

2. The ophthalmologic apparatus of claim 1, further comprising one operation unit configured to receive the input of the instruction to change refractive power applied to the subject's eye, wherein
the control unit is configured to control the refractive power application unit to sequentially apply the measurement value and the one or more refractive values to the subject's eye each time a predetermined operation is performed on the operation unit.

3. The ophthalmologic apparatus of claim 2, wherein the control unit is configured to control the refractive power application unit to cyclically apply the measurement value and the one or more refractive values to the subject's eye each time the predetermined operation is performed on the operation unit.

4. The ophthalmologic apparatus of claim 3, wherein the storage unit is configured to store the one or more refractive values in advance.

5. The ophthalmologic apparatus of claim 3, further comprising an objective measurement unit configured to perform objective measurement for the subject's eye.

6. The ophthalmologic apparatus of claim 3, wherein the one or more refractive values include uncorrected visual acuity of the subject's eye.

7. The ophthalmologic apparatus of claim 3, wherein the one or more refractive values include corrected visual acuity indicating refractive power of a refractive correction worn on the subject's eye.

8. The ophthalmologic apparatus of claim 3, further comprising a visual target present unit configured to present a visual target to the subject's eye.

9. The ophthalmologic apparatus of claim 2, wherein the storage unit is configured to store the one or more refractive values in advance.

10. The ophthalmologic apparatus of claim 2, further comprising an objective measurement unit configured to perform objective measurement for the subject's eye.

11. The ophthalmologic apparatus of claim 2, wherein the one or more refractive values include uncorrected visual acuity of the subject's eye.

12. The ophthalmologic apparatus of claim 2, wherein the one or more refractive values include corrected visual acuity indicating refractive power of a refractive correction worn on the subject's eye.

13. The ophthalmologic apparatus of claim 2, further comprising a visual target present unit configured to present a visual target to the subject's eye.

14. The ophthalmologic apparatus of claim 1, wherein the storage unit is configured to store the one or more refractive values in advance.

15. The ophthalmologic apparatus of claim 1, further comprising an objective measurement unit configured to perform objective measurement for the subject's eye.

16. The ophthalmologic apparatus of claim 1, wherein the one or more refractive values include uncorrected visual acuity of the subject's eye.

17. The ophthalmologic apparatus of claim 1, wherein the one or more refractive values include corrected visual acuity indicating refractive power of a refractive correction worn on the subject's eye.

18. The ophthalmologic apparatus of claim 1, further comprising a visual target present unit configured to present a visual target to the subject's eye.

19. The ophthalmologic apparatus of claim 1, further comprising:
   a visual target present unit configured to present a near vision visual target to a subject's eye, wherein
   the storage unit is configured to store far sight power and near sight power obtained by measurements performed for the subject's eye in a past; and
   the control unit is configured to control the refractive power application unit to alternately apply the far sight power and the near sight power to the subject's eye in response to input of an instruction to change refractive power applied to the subject's eye.

* * * * *